US010913949B2

(12) United States Patent
Ono

(10) Patent No.: US 10,913,949 B2
(45) Date of Patent: Feb. 9, 2021

(54) THERAPEUTIC AGENT FOR SARCOPENIA AND METABOLIC DISEASES

(71) Applicant: NAGASAKI UNIVERSITY, Nagasaki (JP)

(72) Inventor: Yusuke Ono, Nagasaki (JP)

(73) Assignee: NAGASAKI UNIVERSITY, Nagasaki (JP)

( * ) Notice: Subject to any disclaimer, the term of this patent is extended or adjusted under 35 U.S.C. 154(b) by 0 days.

(21) Appl. No.: 15/758,880

(22) PCT Filed: Sep. 9, 2016

(86) PCT No.: PCT/JP2016/076627
§ 371 (c)(1),
(2) Date: Mar. 9, 2018

(87) PCT Pub. No.: WO2017/043630
PCT Pub. Date: Mar. 16, 2017

(65) Prior Publication Data
US 2018/0282733 A1 Oct. 4, 2018

(30) Foreign Application Priority Data

Sep. 11, 2015 (JP) ................................ 2015-179698

(51) Int. Cl.
| | | |
|---|---|---|
| C12N 15/113 | (2010.01) | |
| A61K 31/713 | (2006.01) | |
| A61K 31/7088 | (2006.01) | |
| A61K 39/395 | (2006.01) | |
| A61K 31/7105 | (2006.01) | |
| C07K 16/40 | (2006.01) | |

(52) U.S. Cl.
CPC ...... *C12N 15/1137* (2013.01); *A61K 31/7088* (2013.01); *A61K 31/713* (2013.01); *A61K 31/7105* (2013.01); *A61K 39/395* (2013.01); *C07K 16/40* (2013.01); *C12N 15/113* (2013.01); *A01K 2217/056* (2013.01); *A01K 2227/105* (2013.01); *A01K 2267/0306* (2013.01); *C07K 2317/76* (2013.01); *C12N 2310/11* (2013.01); *C12N 2310/14* (2013.01)

(58) Field of Classification Search
CPC .............. C12N 15/1137; C12N 15/113; C12N 2310/11; C12N 2310/14; A61K 31/713; A61K 31/7088; A61K 39/395; A61K 31/7105; C07K 16/40; C07K 2317/76; A01K 2267/0306; A01K 2227/105; A01K 2217/056; A61P 43/00; A61P 3/10; A61P 3/08; A61P 3/06; A61P 3/00; A61P 21/04; A61P 21/00
See application file for complete search history.

(56) References Cited

U.S. PATENT DOCUMENTS

2009/0280517 A1 11/2009 Bloch et al.

FOREIGN PATENT DOCUMENTS

| JP | 2005-137202 A | 6/2005 |
|---|---|---|
| WO | 2015/064585 A1 | 5/2015 |

OTHER PUBLICATIONS

Bahi et al., "Differential Effects of Thyroid Hormones on Energy Metabolism of Rat Slow- and Fast-Twitch Muscles," *J. Cell Physiol.*, 203(3): 589-598 (2005).
Clément et al., "In Vivo Regulation of Human Skeletal Muscle Gene Expression by Thyroid Hormone," *Genome Res.*, 12(2): 281-291 (2002).
Cohen et al., "Muscle wasting in disease: molecular mechanism and promising therapies," *Nat. Rev. Drug Discov.*, 14(1): 58-74 (2015).
Egerman et al., "Signaling pathways controlling skeletal muscle mass," *Crit. Rev. Biochem. Mol. Biol.*, 49(1): 59-68 (2014).
Kim et al., "μ-Crystallin is a mammalian homologue of *Agrobacterium* ornithine cyclodeaminase and is expressed in human retina," *Proc. Natl. Acad. Sci. USA*, 89(19): 9292-9296 (1992).
Lee et al., "Thyroid Hormone Signaling in Muscle Development, Repair and Metabolism," *J. Endocrinol. Diabetes Obes.*, 2(3): 1046 (2014).
Lek et al., "Emerging preclinical animal models for FSHD," *Trends Mol. Med.*, 21(5): 295-306 (2015).
Mullur et al., "Thyroid Hormone Regulation of Metabolism," *Physiol. Rev.*, 94(2): 355-382 (2014).
Nwoye et al., "Evidence for a direct action of thyroid hormone in specifying muscle properties," *Am. J. Physiol.*, 242(3): R401-R408 (1982).
Reed et al., "Abnormal expression of mu-crystallin in facioscapulohumeral muscular dystrophy," *Exp. Neurol.*, 205(2): 583-586 (2007).
Salvatore et al., "Thyroid hormones and skeletal muscle—new insights and potential implications," *Nat. Rev. Endocrinol.*, 10(4): 206-214 (2014).
Seko et al., "The FSHD-related protein μ-crystallin controls metabolic and contractile properties in skeletal muscle," *Abstracts Neuromuscular Disorders*, 25, Supplement 2: S215, Abstract G.P.97 (2015).

(Continued)

*Primary Examiner* — J. E. Angell
(74) *Attorney, Agent, or Firm* — Leydig, Voit & Mayer, Ltd.

(57) ABSTRACT

The present invention provides a therapeutic agent for a muscle weakness symptom (sarcopenia) or a metabolic disease, containing a μ-crystallin (CRYM) inhibitory substance as an active ingredient. The inhibitory substance is selected from the group consisting of an antisense nucleic acid against CRYM, an RNAi-inducing nucleic acid against CRYM and a ribozyme against CRYM, expression vectors of these, an antagonist antibody against CRYM, and a low molecular weight compound that inhibits activity of CRYM.

11 Claims, 6 Drawing Sheets
Specification includes a Sequence Listing.

(56) References Cited

OTHER PUBLICATIONS

Seko et al., "μ-Crystallin controls muscle function through thyroid hormone action," *FASEB J.*, 30(5): 1733-1740 (2016).
Suzuki et al., "μ-Crystallin as an Intracellular 3,5,3'-Triiodothyronine Holder *in Vivo*," *Mol. Endocrinol.*, 21(4): 885-894 (2007).
Suzuki et al., "Massho Tankakukyu ni Okeru CRYM Indenshi Hatsugen Teiryoho no Kakuritsu to Karei ni Okeru Totaisha tono Kankei," *Japanese Journal of Geriatrics*, 44: 118, Abstract P59 (2007).
Takeshige et al., "Cytosolic T3-binding protein modulates dynamic alteration of T3-mediated gene expression in cells," *Endocr. J.*, 61(6): 561-570 (2014).
Tawil et al., "Facioscapulohumeral dystrophy: the path to consensus on pathophysiology," *Skelet. Muscle*, 4: 12 (2014).
Vanderplanck et al., "The FSHD Atrophic Myotube Phenotype is Caused by DUX4 Expression," *PLoS One*, 6(10): e26820 (2011).
Vié et al., "Purification, Molecular Cloning, and Functional Expression of the Human Nicodinamide-Adenine Dinucleotide Phosphate-Regulated Thyroid Hormone-Binding Protein," *Mol. Endocrinol.*, 11(11): 1728-1736 (1997).
Yamauchi et al., "Effect of coenzymes and thyroid hormones on the dual activities of *Xenopus* cytosolic thyroid-hormone-binding protein (xCTBP) with aldehyde dehydrogenase activity," *Eur. J. Biochem.*, 269(8): 2257-2264 (2002).
Japanese Patent Office, International Search Report in International Patent Application No. PCT/JP2016/076627 (dated Oct. 11, 2016).

THERAPEUTIC AGENT FOR SARCOPENIA AND METABOLIC DISEASES

CROSS-REFERENCE TO RELATED APPLICATIONS

This patent application is the U.S. national phase of International Patent Application No. PCT/JP2016/076627, filed Sep. 9, 2016, which claims the benefit of Japanese Patent Application No. 2015-179698, filed on Sep. 11, 2015, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 44,221 bytes ASCII (Text) file named "738579Sequence-Listing.txt," created Mar. 8, 2018.

TECHNICAL FIELD

The present invention relates to a therapeutic agent for muscle weakness symptoms and metabolic diseases, and relates to a therapeutic agent targeting µ-crystallin molecule for treating both muscle weakness symptoms and metabolic diseases.

BACKGROUND ART

Skeletal muscle is the largest tissue in the human body, accounting for 40-50% of body weight. It is a highly plastic tissue that can readily adapt its contractile and metabolic properties and muscle size in response to a variety of stimuli, such as physical activity. Understanding how muscle plasticity is regulated is a central question in muscle biology and regenerative medicine, with particular relation to the failure of muscle maintenance in muscle diseases such as muscular dystrophies, cancer cachexia, and age-related sarcopenia (non-patent documents 1, 2). Skeletal muscle properties are potentially influenced by circulating hormones and growth factors that possess anabolic or catabolic effects. Thyroid hormone has important roles in an extensive range of physiological functions, such as regulation of normal development, cellular proliferation and differentiation, thermogenesis, homeostasis, and metabolism (non-patent documents 3-5). In skeletal muscle, thyroid hormone plays an important role in conversion to glycolytic fast fiber-type (non-patent documents 4, 6-8).

µ-Crystallin (CRYM) was first identified in the kangaroo eye lens and has been characterized as an NADPH-dependent cytosolic triiodothyronine (T3)-binding protein, regulating "triiodothyronine (T3)" transportation from cytoplasm to the nucleus (non-patent documents 9-11). CRYM positively regulates thyroid hormone action by promoting T3 binding to thyroid hormone receptor-containing dimers, which in turn bind to genomic thyroid-response elements to regulate the expression of thyroid hormone-responsive genes in the nucleus. However, CRYM-deficient mice display normal growth without alteration of peripheral T3 action (non-patent document 12).

Facioscapulohumeral muscular dystrophy (FSHD) is an autosomal dominant disease characterized by a unique pattern of affected muscles, especially accompanied with a reduction of facial and shoulder girdle muscle mass followed by weakness of lower limb muscles (non-patent documents 13, 14). Aberrant high expression of CRYM has been reported in muscles of patients with FSHD, whereas appreciable up-regulation of CRYM has not been observed in several other myopathies and muscular dystrophies (non-patent document 15). Another study suggested that high amounts of CRYM protein are expressed in FSHD muscle-derived myoblasts and that the FSHD-related transcription factor DUX4 directly induces CRYM expression (non-patent document 16). In addition, a method for diagnosing FSHD by using CRYM as a molecule marker is known (patent document 1).

DOCUMENT LIST

Patent Document patent document 1: US2009/0280517 A1

Non-Patent Documents non-patent document 1: Cohen, S., Nathan, J. A., and Goldberg, A. L. (2015) Nature reviews. Drug discovery 14, 58-74
non-patent document 2: Egerman, M. A., and Glass, D. J. (2014) Critical reviews in biochemistry and molecular biology 49, 59-68
non-patent document 3: Lee, J. W., Kim, N. H., and Milanesi, A. (2014) Journal of endocrinology, diabetes & obesity 2, 1046
non-patent document 4: Salvatore, D., Simonides, W. S., Dentice, M., Zavacki, A. M., and Larsen, P. R. (2014) Nature reviews. Endocrinology 10, 206-214
non-patent document 5: Mullur, R., Liu, Y. Y., and Brent, G. A. (2014) Physiological reviews 94, 355-382
non-patent document 6: Clement, K., Viguerie, N., Diehn, M., Alizadeh, A., Barbe, P., Thalamas, C., Storey, J. D., Brown, P. O., Barsh, G. S., and Langin, D. (2002) Genome research 12, 281-291
non-patent document 7: Nwoye, L., Mommaerts, W. F., Simpson, D. R., Seraydarian, K., and Marusich, M. (1982) The American journal of physiology 242, R401-408
non-patent document 8: Bahi, L., Garnier, A., Fortin, D., Serrurier, B., Veksler, V., Bigard, A. X., and Ventura-Clapier, R. (2005) J Cell Physiol 203, 589-598
non-patent document 9: Kim, R. Y., Gasser, R., and Wistow, G. J. (1992) Proceedings of the National Academy of Sciences of the United States of America 89, 9292-9296
non-patent document 10: Vie, M. P., Evrard, C., Osty, J., Breton-Gilet, A., Blanchet, P., Pomerance, M., Rouget, P., Francon, J., and Blondeau, J. P. (1997) Mol Endocrinol 11, 1728-1736
non-patent document 11: Takeshige, K., Sekido, T., Kitahara, J., Ohkubo, Y., Hiwatashi, D., Ishii, H., Nishio, S., Takeda, T., Komatsu, M., and Suzuki, S. (2014) Endocrine journal 61, 561-570
non-patent document 12: Suzuki, S., Suzuki, N., Mori, J., Oshima, A., Usami, S., and Hashizume, K. (2007) Mol Endocrinol 21, 885-894
non-patent document 13: Tawil, R., van der Maarel, S. M., and Tapscott, S. J. (2014) Skeletal muscle 4, 12
non-patent document 14: Lek, A., Rahimov, F., Jones, P. L., and Kunkel, L. M. (2015) Trends in molecular medicine 21, 295-306
non-patent document 15: Reed, P. W., Corse, A. M., Porter, N. C., Flanigan, K. M., and Bloch, R. J. (2007) Experimental neurology 205, 583-586 non-patent document 16: Vanderplanck, C., Ansseau, E., Charron, S., Stricwant, N., Tassin, A., Laoudj-Chenivesse, D., Wilton, S. D., Coppee, F., and Belayew, A. (2011) PloS one 6, e26820

SUMMARY OF THE INVENTION

Problems to be Solved by the Invention

An object of the present invention is to elucidate the physiological function of skeletal muscle and provide a means that particularly contributes to the treatment of diseases accompanied by weakness of muscle or hypometabolism.

Means of Solving the Problems

The present inventor investigated the role of CRYM in skeletal muscle of mice. CRYM-deficient mice displayed muscle hypertrophy of fast-twitch glycolytic-type IIb fibers. Muscle strength and high-intensity exercise performance were upregulated in CRYM-deficient mice. Functional inhibition of CRYM due to CRYM knockout or siRNA-mediated knockdown increased glycolytic contractile properties of myotubes derived from satellite cells in a culture system. These changes were regulated, at least in part, through thyroid hormone action. In summary, the present inventor has found that CRYM is an extremely important regulator of muscle plasticity, which regulates the metabolic and contractile properties of myofibers, which resulted in the completion of the present invention. That is, the present invention is as shown below.

[1] A therapeutic agent for a muscle weakness symptom (sarcopenia) or a metabolic disease, comprising a μ-crystallin (CRYM) inhibitory substance as an active ingredient.
[2] The therapeutic agent of [1], wherein the CRYM inhibitory substance is selected from the group consisting of an antisense nucleic acid against CRYM, an RNAi-inducing nucleic acid against CRYM and a ribozyme against CRYM, expression vectors of these, an antagonist antibody against CRYM, and a low molecular weight compound that inhibits activity of CRYM.
[3] The therapeutic agent of [1] or [2], wherein the muscle weakness symptom is primary sarcopenia, activity-related sarcopenia, disease-related sarcopenia or nutrition-related sarcopenia, and the metabolic disease is a metabolic disease associated with the aforementioned sarcopenia.
[4] The therapeutic agent of any of [1] to [3], wherein the metabolic disease is a disorder of carbohydrate metabolism or a disorder of lipid metabolism.
[5] A method for treating a muscle weakness symptom (sarcopenia) or a metabolic disease, comprising administering an effective amount of a CRYM inhibitory substance to a subject in need thereof.
[6] The treatment method of [5], wherein the CRYM inhibitory substance is selected from the group consisting of an antisense nucleic acid against CRYM, an RNAi-inducing nucleic acid against CRYM and a ribozyme against CRYM, expression vectors of these, an antagonist antibody against CRYM, and a low molecular weight compound that inhibits activity of CRYM.
[7] The treatment method of [5] or [6], wherein the muscle weakness symptom is selected from the group consisting of primary sarcopenia, activity-related sarcopenia, disease-related sarcopenia and nutrition-related sarcopenia and the aforementioned sarcopenia associated with a metabolic disease.
[8] The treatment method of any of [5]-[7], wherein the metabolic disease is a disorder of carbohydrate metabolism or a disorder of lipid metabolism.
[9] Use of a CRYM inhibitory substance in the production of a therapeutic agent for the muscle weakness symptom (sarcopenia) or the metabolic disease of any of [1]-[4].
[10] A CRYM inhibitory substance for use in the treatment of a muscle weakness symptom (sarcopenia) or a metabolic disease.
[11] A CRYM inhibitory substance for use in the treatment of a muscle weakness symptom (sarcopenia) or a metabolic disease, which substance is selected from the group consisting of an antisense nucleic acid against CRYM, an RNAi-inducing nucleic acid against CRYM and a ribozyme against CRYM, expression vectors of these, an antagonist antibody against CRYM, and a low molecular weight compound that inhibits activity of CRYM.
[12] The CRYM inhibitory substance of [10] or [11], wherein the muscle weakness symptom is primary sarcopenia, activity-related sarcopenia, disease-related sarcopenia or nutrition-related sarcopenia, and the metabolic disease is a metabolic disease associated with the aforementioned sarcopenia.
[13] The CRYM inhibitory substance of any of [10]-[12], wherein the metabolic disease is a disorder of carbohydrate metabolism or a disorder of lipid metabolism.

Effect of the Invention

The therapeutic agent of the present invention for a muscle weakness symptom or a metabolic disease has an action to significantly suppress a decrease in the metabolism and muscle force, improve metabolism or enhance muscle force (particularly type II fast muscle) by regulating thyroid hormone action by targeting Crym in the skeletal muscle, and is particularly useful for the treatment of sarcopenia and/or a disorder of carbohydrate metabolism.

DESCRIPTION OF EMBODIMENTS

Figure 1:
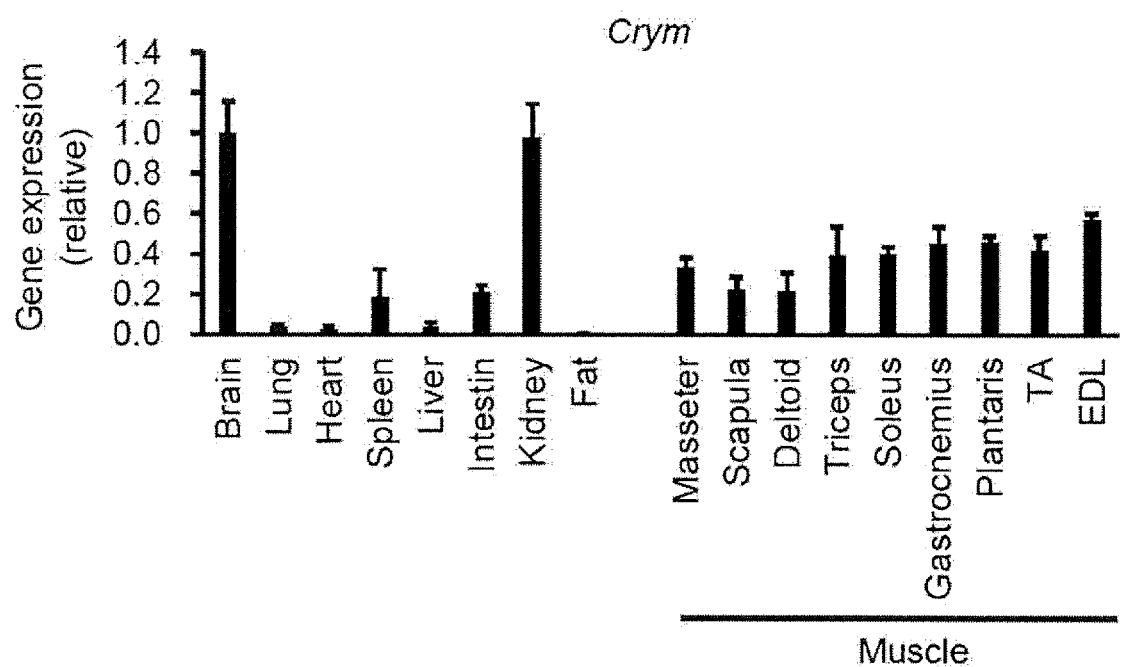
FIG. 1 shows that Crym is expressed in adult skeletal muscle. (A) Expression profile of Crym mRNA in the entire body of adult mice by Q-PCR analysis is shown (subscapularis muscle, Scapula; tibialis anterior, TA; extensor digitorum longus, EDL) (n=3 mice). (B) Satellite cells isolated from mice EDL muscles were cultured in mitogen-rich medium (GM) for 6 days, and myogenic differentiation was induced in serum-reduced medium (DM) for 3 days. Q-PCR analysis of Crym expression in primary culture satellite cells under myogenic progression (upper panel, bright field; lower panel, gene expression level) (n=3 mice). The data is shown in mean±SEM.
Figure 1:
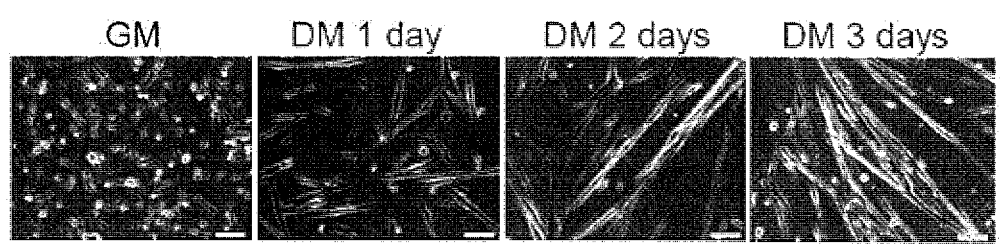
Figure 1:
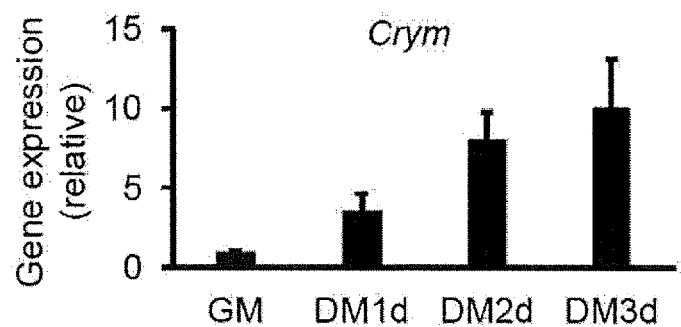

The therapeutic agent of the present invention characteristically contains a μ-crystallin inhibitory substance as an active ingredient.

In the present invention, μ-crystallin refers to a protein that regulates transport of triiodothyronine (T3) from the cytoplasm to the nucleus, and is also referred to as a NADPH-dependent cytosolic T3-binding protein (CTBP). In the present specification, it is abbreviated as "CRYM" or "Crym".

The gene encoding CRYM may have a base sequence derived from any animal. For example, a human CRYM gene is preferable for the development of a therapeutic agent for human. When a mouse, which is easily utilizable as an experiment animal, is used, the analysis results in mouse are sufficiently expected to reflect the pathology in other mammals including human. Thus, use of a mouse CRYM gene is also preferable. In the present specification, the human CRYM gene has, as the standard, the base sequence (SEQ ID NO: 1) publicly reported under Genbank Accession No. NM_001888.4. In addition, the mouse CRYM gene has, as the standard, the base sequence (SEQ ID NO: 3) publicly reported under Genbank Accession No. NM_016669.1. The rat CRYM gene has, as the standard, the base sequence (SEQ ID NO: 5) publicly reported under Genbank Accession No. NM_053955.1. The monkey CRYM gene has, as the standard, the base sequence (*Macaca mulatta*: SEQ ID NO: 7) publicly reported under Genbank Accession No. NM_001266891.1 or the base sequence (*Macaca fascicularis*: SEQ ID NO: 9) publicly reported under Genbank Accession No. NM_001287652.1. CRYM homologues derived from other animals can be identified by HomoloGene (http://www.ncbi.nlm.nih.gov/HomoloGene/). Concretely, a particular human base sequence is applied to BLAST (Proc. Natl. Acad. Sci. USA 90:5873-5877, 1993, http://www.ncbi.nlm.nih.gov/BLAST/) and the accession number of the sequence which matches (the highest Score, E-value is 0 and Identity is 100%) is obtained. The accession number is input into UniGene (http://www.ncbi.nlm.nih.gov/UniGene/) and the obtained UniGene Cluster ID (number shown with Hs.) is input into HomoloGene. From the list showing the correlation in the gene homologues between the genes of other species and human gene obtained as the result, genes of other species can be selected as genes (homologs) corresponding to the human genes represented by the particular base sequence.

Similarly, the human CRYM protein in the present invention has, as the standard, the amino acid sequence (SEQ ID NO: 2) publicly reported under Genbank Accession No. NP_001879.1. In addition, the mouse CRYM protein has, as the standard, the amino acid sequence (SEQ ID NO: 4) publicly reported under Genbank Accession No. NP_057878.1. The rat CRYM protein has, as the standard, the amino acid sequence (SEQ ID NO: 6) publicly reported under Genbank Accession No. NP_446407.1. The monkey CRYM protein has, as the standard, the amino acid sequence (*Macaca mulatta*: SEQ ID NO: 8) publicly reported under Genbank Accession No. NP_001253820.1 or the amino acid sequence (*Macaca fascicularis*: SEQ ID NO: 10) publicly reported under Genbank Accession No. NP_001274581.1.

In the present invention, the CRYM inhibitory substance is a generic term for a substance that inhibits expression of CRYM and a substance that inhibits activity of CRYM. Substance that inhibits activity of CRYM includes a substance that inhibits the activity by interacting with CRYM, a substance that inhibits binding of CRYM and T3 and the like.

The substance that inhibits expression of CRYM can be selected by measuring the expression level of mRNA or protein of CRYM in CRYM expressing cells and confirming a significant decrease in the expression level as compared with that of a control free of addition. The substance that inhibits activity of CRYM can be selected by adding the substance to a system containing CRYM and T3 (labeled T3) and confirming a significant decrease in the binding of CRYM and T3 as compared with that of a control free of addition.

Concrete examples of the CRYM inhibitory substance include those selected from the group consisting of an antisense nucleic acid against CRYM, an RNAi-inducing nucleic acid against CRYM and a ribozyme against CRYM, expression vectors of these, an antagonist antibody against CRYM, and a low molecular weight compound that inhibits activity of CRYM. These may be natural substances or artificially-synthesized substances.

The aforementioned antisense nucleic acid against CRYM consists of a base sequence hybridizable with a transcription product of CRYM (mRNA or initial transcription product) under physiological conditions of cells that express the transcription product, and is a polynucleotide capable of inhibiting, in a hybridized state, translation of polypeptide encoded by the transcription product. As the kind of the antisense nucleic acid, it may be DNA or RNA, or DNA/RNA chimera. The antisense nucleic acid may have a non-modified (natural-type) phosphodiester bond or a chemically-modified nucleotide such as thiophosphoric acid type (P=O of phosphate bond is substituted by P=S) stable to degrading enzymes, 2'-O-methyl type and the like. As other elements important for designing an antisense nucleic acid, enhancement of water solubility and cell membrane permeability and the like can be mentioned. However, these can also be achieved by modifying the dosage form by using a liposome or microsphere and the like. The length of the antisense nucleic acid is not particularly limited as long as it can specifically hybridize with the transcription product of CRYM (e.g., mRNA corresponding to the base sequence of SEQ ID NO: 1, 3, 5, 7 or 9). A shorter length may be about 6 bases and a longer length may be a sequence containing a sequence complementary to the whole sequence of the transcription product. In view of the easiness of synthesis and antigenicity, for example, an oligonucleotide consisting of not less than about 6 bases, preferably about 15-about 40 bases, more preferably about 15 bases-about 30 bases can be recited as examples. Furthermore, the antisense nucleic acid may be not only one that inhibits translation by hybridizing with the transcription product of CRYM, but also one capable of inhibiting transcription to mRNA by binding to double-stranded DNA to form a triple strand (triplex).

In the present specification, being "complementary" means that base sequences have a complementarity of about 70% or more, preferably about 80% or more, more preferably about 90% or more, further preferably about 95% or more, most preferably 100%, among the base sequences. The complementarity of the base sequences in the present specification can be calculated using the homology calculation algorithm NCBI BLAST (National Center for Biotechnology Information Basic Local Alignment Search Tool) under the following conditions (expect=10; gap allowed; filtering=ON; match score=1; mismatch score=−3).

The complementarity of the antisense nucleic acid does not necessarily need to be 100% and it may be of a level sufficient to achieve complementary binding to DNA or RNA of CRYM in vivo.

The aforementioned RNAi-inducing nucleic acid refers to a polynucleotide capable of inducing RNA interference by being introduced into the cell, and is preferably RNA or a chimera molecule of RNA and DNA. RNA interference means an effect of RNA having a double-stranded structure containing the same base sequence (or partial sequence thereof) as mRNA to suppress expression of the mRNA. To achieve the RNAi effect, for example, RNA having a double-stranded structure containing at least 19 contiguous base sequences (or partial sequences thereof), which are the same as those of the target mRNA, is preferably used. However, several bases may be substituted as long as the expression inhibitory action of CRYM is present, and may be RNA shorter in length than 19 bases. The double-stranded structure may be composed of different strands of a sense strand and an antisense strand, or may be a double strand (shRNA) achieved by a stem loop structure of one RNA. Examples of the RNAi-inducing nucleic acid include siRNA, miRNA and the like. miRNA recognizes 3'UTR of CRYM gene and unstabilizes the target mRNA, and also suppresses expression of CRYM by suppressing translation.

The RNAi-inducing nucleic acid is preferably siRNA since it shows a strong transcription suppressive activity. The siRNA against Crym can target any portion of mRNA of CRYM. While the siRNA molecule against CRYM is not particularly limited as long as it can induce RNAi effect, it is, for example, 18-27 bases in length, preferably 21-25 bases in length. The siRNA against Crym is a double strand containing a sense strand and an antisense strand. Concretely, the siRNA against Crym consists of a sense strand containing 18-25 contiguous base sequences in mRNA corresponding to the base sequence of SEQ ID NO: 1, 3, 5, 7 or 9, and an antisense strand containing a complementary sequence thereof. The siRNA against Crym optionally has overhang at the 5'-terminal or 3'-terminal of one or both of the sense strand and the antisense strand. The overhang is formed by the addition of 1—several (e.g., 1, 2 or 3) bases at the terminal of the sense strand and/or the antisense strand. A method for designing siRNA is known to those of ordinary skill in the art, and an appropriate base sequence of siRNA can be selected from the above-mentioned base sequences by using various design softwares or algorithms of siRNA.

The aforementioned "ribozyme" refers to RNA having enzymatic activity for cleaving nucleic acid. Recently, it has been clarified that oligo DNA having a base sequence of the enzyme active site similarly has enzymatic activity for cleaving nucleic acid. In the present specification, therefore, it is used as a concept encompassing even DNA as long as it has a sequence specific enzymatic activity for cleaving nucleic acid. Concretely, ribozyme can specifically cleave mRNA encoding CRYM or the initial transcription product within the coding region (including the intron site in the case of the initial transcription product). One of the most versatile ribozymes is self-splicing RNA found in infectious RNAs such as viroid and virusoid, and hammerhead type, hairpin type and the like are known. The hammerhead type exhibits enzyme activity with about 40 bases in length, and it is possible to specifically cleave only the target mRNA by making several bases (about 10 bases in total) at both ends flanking to the hammerhead structure portion a sequence complementary to the desired cleavage site of the mRNA. Furthermore, when ribozyme is used in the form of an expression vector containing DNA encoding same, the ribozyme may be a hybrid ribozyme prepared by further joining a sequence modified from the tRNA to promote the translocation of the transcription product to cytoplasm (Nucleic Acids Res., 29(13): 2780-2788 (2001)).

The CRYM inhibitory substance can also be provided as an expression vector. Such expression vector includes a polynucleotide encoding a CRYM inhibitory substance and a promoter operably linked to the polynucleotide.

The aforementioned promoter can be appropriately selected according to the kind of the nucleic acid of the expression target under regulation thereof. For example, polIII promoter (e.g., tRNA promoter, U6 promoter, H1 promoter), promoters for mammals (e.g., CMV promoter, CAG promoter, SV40 promoter) can be mentioned.

The expression vector of the present invention may further contain a selection marker gene (gene imparting resistant to drugs such as tetracycline, ampicillin, kanamycin, hygromycin, phosphinothricin and the like, gene complementing auxotrophic mutation etc.).

The backbone of the expression vector of the present invention is not particularly limited as long as it can produce a CRYM inhibitory substance in the cells of a mammal such as human and the like. For example, plasmid vector, virus vector can be mentioned. As a vector preferable for administration to a mammal, virus vectors such as retrovirus, adenovirus, adeno-associated virus, herpes virus, vaccinia virus, pox virus, polio virus, sindbis virus, Sendai virus and the like can be mentioned. Of these, virus vectors derived from retrovirus, adenovirus, adeno-associated virus, vaccinia virus are preferable.

The aforementioned CRYM antagonist antibody refers to an antibody that specifically binds to CRYM and inhibits the activity of CRYM by binding thereto.

In the present specification, examples of the antibody include natural-type antibodies such as polyclonal antibody, monoclonal antibody and the like, chimeric antibodies produced using a gene recombinant technique, humanized antibody, single-stranded antibody, human antibodies that can be produced using a human antibody-producing transgenic animal, antibodies produced by phage display and binding fragments of these.

The binding fragment means a partial region of the above-described antibodies; concretely including, for example, F(ab')$_2$, Fab', Fab, Fv (variable fragment of antibody), sFv, dsFv (disulphide stabilized Fv), dAb (single domain antibody) and the like (Exp. Opin. Ther. Patents, Vol. 6, No. 5, p. 441-456, 1996).

The class of antibody is not particularly limited, and any antibody having any isotype such as IgG, IgM, IgA, IgD, IgE or the like is also encompassed. Preferred is IgG or IgM and, in consideration of the easiness of the purification and the like, more preferred is IgG.

Polyclonal antibody and monoclonal antibody can be produced by a known general production method. That is, for example, in the case of a polyclonal antibody, a mammal, for example, mouse, rat, hamster, guinea pig, rabbit, cat, dog, pig, goat, horse, bovine or the like, preferably mouse, rat, hamster, guinea pig, goat, horse or rabbit, is immunized with an immunogen together with Freund's adjuvant as necessary. In the case of a monoclonal antibody, mouse, rat, hamster and the like are immunized.

Polyclonal antibody can be specifically produced as follows. That is, mouse, rat, hamster, guinea pig, goat, horse or rabbit, preferably goat, horse or rabbit, more preferably rabbit, is immunized by subcutaneous, intramuscular, intravenous, intrafootpad or intraperitoneal injection of an immunogen 1—several times. Generally, immunization is performed 1-5 times every about 1-14 days from the initial immunization, and the serum is obtained from the immunologically sensitized mammal about 1-5 days from the final immunization.

While serum can also be used as a polyclonal antibody, an antibody is preferably isolated and/or purified by ultrafiltration, ammonium sulfate fraction, euglobulin precipitation, caproinic acid method, caprylic acid method, ion exchange chromatography (DEAE or DE52 etc.), affinity column chromatography using an anti-immunoglobulin column or protein A/G column, an immunogen crosslinked column and the like.

The monoclonal antibody is produced by preparing a hybridoma from antibody-producing cells obtained from the above-mentioned immunologically sensitized animal and myeloma-series cell (myeloma cell) without an autoantibody producing ability, cloning the hybridoma, and selecting a clone that produces a monoclonal antibody showing specific affinity for the immunogen used for immunizing mammal.

To be specific, the monoclonal antibody can be produced as follows. That is, mouse, rat or hamster (including transgenic animal generated to produce an antibody derived from other animal such as human antibody-producing transgenic mouse) is immunized by subcutaneous, intramuscular, intravenous, intrafootpad or intraperitoneal injection 1—several times or transplantation of an immunogen. Generally, immunization is performed 1-4 times every about 1-14 days from the initial immunization, and the antibody-producing cells are obtained from the immunologically sensitized mammal about 1-5 days from the final immunization.

The hybridoma (fusion cell) that secretes a monoclonal antibody can be prepared by the method of Köhler and Milstein et al. (Nature, Vol. 256, p. 495-497, 1975) and a modified method according thereto. That is, the hybridoma is prepared by cell fusion of antibody-producing cells contained in the spleen, lymph node, bone marrow, tonsil etc., preferably spleen, the obtained from a mammal immunized as mentioned above, and myeloma cells free of an autoantibody producing ability, which are derived from a mammal preferably mouse, rat, guinea pig, hamster, rabbit, human and the like, more preferably mouse, rat or human.

As the myeloma cells to be used for cell fusion, myeloma P3/X63-AG8.653 (653; ATCC No. CRL1580), P3/NSI/1-Ag4-1 (NS-1), P3/X63-Ag8.U1 (P3U1), SP2/0-Ag14 (Sp2/0, Sp2), PAI, F0 or BW5147 derived from mouse, myeloma 210RCY3-Ag.2.3. derived from rat, myeloma U-266AR1, GM1500-6TG-A1-2, UC729-6, CEM-AGR, D1R11 or CEM-T15 derived from human can be used.

A hybridoma clone producing a monoclonal antibody can be screened for by culturing the hybridoma in, for example, a microtiter plate, measuring the reactivity of the culture supernatant, in the well showing growth, to the immunogen used for the aforementioned immunization by, for example, an enzyme immunoassay such as ELISA and the like.

The aforementioned hybridoma is cultured in a medium (e.g., DMEM containing 10% bovine calf serum). A centrifuged supernatant of the culture broth can be used as a monoclonal antibody solution. By injecting the hybridoma into the abdominal cavity of an animal from which the hybridoma is derived, ascites is produced, and the obtained ascites can be used as a monoclonal antibody solution. Monoclonal antibody is preferably isolated and/or purified similarly to the aforementioned polyclonal antibody.

Chimeric antibody can be produced by reference to, for example, "Jikken Igaku (extra issue), Vol. 6, No. 10, 1988", JP-B-3-73280 and the like, humanized antibody can be produced by reference to, for example, JP-A-4-506458, JP-A-62-296890 and the like, and human antibody can be produced by reference to, for example, "Nature Genetics, Vol. 15, p. 146-156, 1997", "Nature Genetics, Vol. 7, p. 13-21, 1994", JP-A-4-504365, WO 94/25585, "Nikkei Science, June issue, pages 40-50, 1995", "Nature, Vol. 368, p. 856-859, 1994", JP-A-6-500233 and the like.

An antibody by phage display can be produced by, for example, recovering and concentrating a phage having affinity for antigen by biopanning from a phage library prepared for screening human antibody, whereby antibody such as Fab and the like, and the like can be obtained easily. As to the production of antibody by phage display, refer to "Nature, Vol. 348, p. 552-554, 1990", "Phage display a laboratory manual" In cold spring harbor laboratory press, 2001", "Antibody Engineering—a Practical Approach, IRL Press, Oxford, 1996".

F(ab')$_2$ and Fab' can be respectively produced by treating immunoglobulin with pepsin and papain, which are proteases. Fab can be produced by screening the Fab expression phage library similarly to the above-mentioned method for antibody preparation by phage display.

In the present invention, the low molecular weight compound that inhibits activity of CRYM is a concept including even a salt thereof and a solvate thereof.

Examples of the salt include pharmacologically acceptable salts, for example, salt with inorganic acid, salt with organic acid, salt with basic or acidic amino acid and the like.

Examples of the salt with inorganic acid include salts with hydrochloric acid, hydrobromic acid, nitric acid, sulfuric acid, phosphoric acid and the like.

Examples of the salt with organic acid include salts with benzoic acid, formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Examples of the salt with basic amino acid include salts with arginine, lysine, ornithine and the like, and preferable examples of the salt with acidic amino acid include salts with aspartic acid, glutamic acid and the like.

Preferable examples of the solvate include hydrate (e.g., monohydrate, dihydrate and the like), ethanolate and the like.

The target diseases of the therapeutic agent of the present invention are muscle weakness symptoms and metabolic diseases. The muscle weakness symptom is a muscle disease caused by high expression of CRYM in the skeletal muscle. The metabolic disease refers to a disorder of lipid metabolism, a disorder of carbohydrate metabolism, proteometabolism abnormality or a disorder of nucleic acid metabolism.

As the muscle weakness symptom in the present invention, sarcopenia is a particular treatment target. As the metabolic disease in the present invention, a metabolic disease associated with sarcopenia is the treatment target. In the present invention, the "treatment" is a concept including not only the treatment after the onset but also the prophylaxis of the disease.

In the present invention, sarcopenia is a syndrome characterized by progressive and generalized loss of skeletal muscle mass and strength with a risk of adverse outcomes such as physical disability, poor quality of life and death (European Working Group on Sarcopenia in Old People: definition by EWGSOP). Sarcopenia can be classified according to its cause and includes primary sarcopenia, activity-related sarcopenia, disease-related sarcopenia and nutrition-related sarcopenia. The primary sarcopenia refers to sarcopenia without any cause other than aging and is also referred to as age-related sarcopenia. The activity-related sarcopenia refers to sarcopenia caused by bed rest, sedentary lifestyle, deconditioning or zero-gravity conditions. The disease-related sarcopenia refers to sarcopenia caused by advanced organ failure (heart, lung, liver, kidney, brain), inflammatory disease, malignancy or endocrine disease. The nutrition-related sarcopenia refers to sarcopenia caused by malabsorption, gastrointestinal disorders, use of medications that cause anorexia or insufficient dietary intake of protein.

The diagnostic criteria (EWGSOP) of sarcopenia include concurrent presence of a decrease in either muscular strength or muscle function (body movement and the like), while presupposing the presence of a decrease in the muscle mass. For the measurement of muscle mass, a dual energy X-ray absorptiomtry (DXA method) or a bioimpedance method (BIA method) is recommended. For the assessment of muscle force, grip strength measurement is recommended and, for the assessment of muscle function, measurement of gait speed is recommended.

Administration of the therapeutic agent of the present invention promotes expression of glycolytic enzymes in the skeletal muscle. Among the metabolic diseases, therefore, a disorder of carbohydrate metabolism is preferably set as the target. Since a disorder of carbohydrate metabolism also relates to a disorder of lipid metabolism, it is preferable to also set a disorder of lipid metabolism as the target. A representative example of the disorder of carbohydrate metabolism is diabetes. A representative example of the disorder of lipid metabolism is hyperlipidemia (dyslipidemia).

The therapeutic agent of the present invention can be administered orally or parenterally to a patient. As the administration form, oral administration, topical administration, intravenous administration, transdermal administration and the like can be mentioned. Where necessary, it is formulated together with pharmaceutically acceptable additives into a dosage form suitable for the administration. Examples of the dosage form suitable for the oral administration include tablet, capsule, granule, powder and the like, and examples of the dosage form suitable for the parenteral administration include injection, ointment, lotion, cream, patch and the like. These can be prepared using general techniques widely used in the pertinent field. The administration route and the dosage form of the therapeutic agent of the present invention are not particularly limited as long as the aforementioned treatment effects can be afforded. A preferable administration route is topical administration and the dosage form therefor is injection, ointment, lotion, cream or patch.

In addition to these preparations, the therapeutic agent of the present invention can also be formulated as a preparation for DDS (drug delivery system) such as a preparation for implantation into the organ, microsphere and the like.

To deliver the therapeutic agent of the present invention to a desired tissue (e.g., muscle tissue), not only topical administration such as intramuscular topical administration, subcutaneous topical administration, direct application, adhesion etc. to the skin but also systemic administration such as intravenous injection (drip infusion), subcutaneous administration and the like may be performed.

The therapeutic agent of the present invention may contain a pharmaceutically acceptable carrier according to the kind and administration route of a CRYM inhibitory substance as the active ingredient. Those of ordinary skill in the art can appropriately select a carrier appropriate for the situation. Examples of the carrier that may be selected include, but are not limited to, excipients such as sucrose, starch, mannit, sorbit, lactose, glucose, cellulose, talc, calcium phosphate, calcium carbonate and the like; binders such as cellulose, methylcellulose, hydroxypropylcellulose, polypropylpyrrolidone, gelatin, gum arabic, polyethylene glycol, sucrose, starch and the like; disintegrants such as starch, carboxymethylcellulose, hydroxypropylstarch, sodium-glycol-starch, sodium hydrogen carbonate, calcium phosphate, calcium citrate and the like; lubricants such as magnesium stearate, aerogel, talc, sodium lauryl sulfate and the like; preservatives such as sodium benzoate, sodium bisulfite, methylparaben, propylparaben and the like; pH adjusters such as citric acid, sodium citrate, acetic acid and the like; suspending agents such as methylcellulose, polyvinylpyrrolidone, aluminum stearate and the like; dispersing agents such as surfactant and the like; dissolving agents such as water, physiological saline, ethanol, propylene glycol and the like; isotonicity agents such as glucose, sodium chloride, potassium chloride and the like; base waxes such as cacao butter, polyethylene glycol, refined kerosene and the like, and the like. These carriers are not limited to show a single action and can be used to exert multiple actions.

For example, when the therapeutic agent of the present invention is used as injection, ointment, lotion, cream or patch, stabilizers (e.g., sodium bisulfite, sodium thiosulfate, sodium edetate, sodium citrate, ascorbic acid, dibutylhydroxytoluene and the like), solubilizing agents (e.g., glycerol, propylene glycol, macrogol, polyoxyethylene hydrogenated castor oil and the like), suspending agents (e.g., polyvinylpyrrolidone, hydroxypropylmethylcellulose, hydroxymethylcellulose, sodium carboxymethylcellulose and the like), emulsifiers (e.g., polyvinylpyrrolidone, soybean lecithin, egg-yolk lecithin, polyoxyethylene hydrogenated castor oil, polysorbate 80 and the like), buffers (e.g., phosphate buffer, acetate buffer, borate buffer, carbonate buffer, citrate buffer, tris buffer, glutamic acid, epsilon-aminocaproic acid and the like), thickeners (e.g., water-soluble cellulose derivatives such as methylcellulose, hydroxyethylcellulose, hydroxypropylmethylcellulose, carboxymethylcellulose and the like, sodium chondroitin sulfate, sodium hyaluronate, carboxyvinyl polymer, polyvinyl alcohol, polyvinylpyrrolidone, macrogol and the like), preservatives (e.g., benzalkonium chloride, benzethonium chloride, chlorhexidine gluconate, chlorobutanol, benzyl alcohol, sodium dehydroacetate, paraoxybenzoate, sodium edetate, boric acid and the like), isotonicity agents (e.g., sodium chloride, potassium chloride, glycerol, mannitol, sorbitol, boric acid, glucose, propylene glycol and the like), pH adjusters (e.g., hydrochloric acid, sodium hydroxide, phosphoric acid, acetic acid and the like), algefacients (e.g., 1-menthol, d-camphor, d-borneol, peppermint oil and the like), ointment bases (e.g., white petrolatum, purified lanolin, liquid paraffin, vegetable oils (olive oil, camellia oil, peanuts oil and the like) and the like) and the like can be added as additives. While the amounts of these additives to be added vary depending on the kind, use and the like of the additives to be added, they may be added at concentrations capable of achieving the object of the additives.

The therapeutic agent of the present invention can also be formulated using a nucleic acid such as antisense nucleic acid and the like by a lipofection method. Generally, a liposome composed of phosphatidylserine is used for a lipofection method. Since phosphatidylserine has a negative charge, a cationic lipid, N-[1-(2,3-dioleyloxy)propyl]-N,N,N-triethylammonium chloride (DOTMA) (trade name: TRANSFECTAM, Lipofectamine), which easily affords a stabler liposome, is preferably used as a substitute for phosphatidylserine. When a complex of these cationic lipids and nucleic acid having a negative charge is formed, the liposome charged positively as a whole adsorbs to the surface of a cell charged negatively and can be fused with the cellular membrane, whereby the nucleic acid can be introduced into the cell.

The proportion of the aforementioned active ingredient contained in the therapeutic agent of the present invention can be appropriately determined within the range capable of affording a desired effect. It is generally 0.01-100 wt %, preferably 0.1-99.9 wt %, more preferably 0.5-99.5 wt %.

While the dose of the therapeutic agent of the present invention varies depending on the kind of the active ingredient and the body weight, age, symptom and the like of the subject of administration and cannot be determined automatically, it can be selected from 0.0001 mg to 1000 mg per 1 kg body weight for one dose.

As the subject of administration of the therapeutic agent of the present invention, mammals such as mouse, rat, hamster, guinea pig, rabbit, cat, dog, bovine, horse, sheep, monkey, human and the like can be mentioned.

While the number of administration of the therapeutic agent of the present invention is not particularly limited, it is generally about 1-5 times per day. The dosing period may be short such as several days to about one week or long such as about several weeks to several months. When the aforementioned diseases recur with a considerable interval, the therapeutic agent of the present invention can be administered again.

EXAMPLES

The present invention is explained in more detail in the following by referring to Examples. The present invention is not limited by these Examples in any manner.

(Antibodies and Reagents)

Antibodies and reagents were obtained from the following sources.

Mouse anti-type IIa myosin heavy chain (MyHC) (SC-71) and mouse anti-type IIb MyHC (BF-F3) antibodies were obtained from Deutsche Sammlung von Mikroorganismen (Braunschweig, Germany).

Mouse anti-μ-crystallin antibody was purchased from Santa Cruz Biotechnology (Santa Cruz, Calif., USA).

Mouse anti-tubulin antibody, 2-mercapto-1-methylimidazole (MMI) and 3,3',5-triiodo-L-thyronine sodium salt (T3) were purchased from Sigma-Aldrich (St. Louis, Mo., USA).

A mounting medium with DAPI for nuclear staining and M.O.M. kit were purchased from Vector Laboratories (Burlingame, Calif., USA).

(Animals)

Animal experimentation was examined and approved by the Experimental Animal Care and Use Committee of the Nagasaki University. The Crym−/− mouse strain (Imai, H., Ohta, K., Yoshida, A., Suzuki, S., Hashizume, K., Usami, S., and Kikuchi, T. (2010) Investigative ophthalmology & visual science 51, 3554-3559) was provided by Riken BRC (RBRC04396). B6. 129 genetic background mice were used between 6-13 wk of age, with age-matched littermate controls.

(Induction of Hyperthyroidism and Hypothyroidism in Animal)

Hyperthyroidism was induced by providing drinking water containing T3 (5 μg/ml) for 2 wk. Hypothyroidism was induced by providing drinking water containing 0.1% MMI for 21 d.

(Grip Strength Measurement and Running Test)

Maximum limb muscle force was measured by a grip strength meter (Columbus Instruments, Columbus, Ohio, USA). Three sets of 10 successive measurements were performed, to assess forelimb/hindlimb grip strength. The mean maximum strength in each set of experiments was used for data analysis.

The mice performed a treadmill-running test on an MK-680 treadmill (Muromachi Kikai Co., Ltd., Tokyo, Japan) with a 15° incline at an initial velocity of 10 m/min for 10 min.

After a rest for 10 min after the initial run, velocity was increased by 5 m/min every 2 min in high-speed running tests. In low-speed running tests, velocity was increased by 1 m/min every 3 min.

Exhaustion time points were used as the running times for data analysis.

(Isolation and Culture of Satellite Cells)

According to a previous report (Ono, Y., Masuda, S., Nam, H. S., Benezra, R., Miyagoe-Suzuki, Y., and Takeda, S. (2012) Journal of cell science 125, 1309-1317), extensor digitorum longus (EDL) muscles were isolated and digested in type I collagenase. Satellite cells were obtained from isolated myofibers and cultured in growth medium (GM; GlutaMax DMEM, supplemented with 30% FBS, 1% chicken embryo extract, 10 ng/ml basic fibroblast growth factor and 1% penicillin-streptomycin) at 37° C. in 5% $CO_2$. Myogenic differentiation was induced in differentiation medium (DM; GlutaMax DMEM supplemented with 5% horse serum and 1% penicillin-streptomycin) at 37° C. in 5% $CO_2$.

(transfection of siRNA)

Transfection of siRNA was performed according to a previous report (Ono, Y., Urata, Y., Goto, S., Nakagawa, S., Humbert, P. O., Li, T. S., and Zammit, P. S. (2015) Cell reports 10, 1135-1148). Cells were plated in 6-well plates, and siRNA transfection was performed at 30040% confluence. siRNA duplexes (Stealth siRNA; Life Technologies, Tokyo, Japan) were diluted with OptiMEM (Life Technologies), added at 10 pmol per well and incubated according to the manufacturer's instructions together with RNAiMAX (Life Technologies) diluted with OptiMEM. The following siRNA sequences were used:

```
Crym siRNA-1:
              (sense strand: SEQ ID NO: 11)
5'-UCCAAGCUCAGCAAAGAUGUCAGCC-3'
```

```
Crym siRNA-2:
              (sense strand: SEQ ID NO: 12)
5'-UAACUUGGUGGUGAGCGCAUCCUCA-3'
```

Control siRNA selected by Life Technologies.

(Q-PCR)

Total RNA was extracted from cultured satellite cells or muscle tissues using an RNeasy Kit (Qiagen, Hilden, Germany) or ISOGEN II (NipponGene, Tokyo, Japan), respectively, and cDNA was prepared with a ReverTra Ace kit and genomic DNA remover (Toyobo, Tokyo, Japan). Q-PCR was performed with THUNDERBIRD SYBR qPCR mix and a CFX96 Touch real-time PCR detection system (Bio Rad, Tokyo, Japan).

TABLE 1 primer sequence

| gene name | Forward | Reverse |
| --- | --- | --- |
| TATA box binding protein (standard) | 5'-CAGATGTGCGTCAGGCGTTC-3' (SEQ ID NO: 13) | 5'-TAGTGATGCTGGGCACTGCG-3' (SEQ ID NO: 14) |
| Crym | 5'-ATGCGCTCACCACCAAGTTA-3' (SEQ ID NO: 15) | 5'-ATTTCCATCCATGACCGCCA-3' (SEQ ID NO: 16) |
| muscle type phosphofructokinase (Pfkm) | 5'-GCGGCGGAGGAGAGCTAAAA-3' (SEQ ID NO: 17) | 5t-GGCAGCATTCATACCTTGGGC-3' (SEQ ID NO: 18) |
| lactate dehydrogenase A (LDH) | 5'-TAATGAAGGACTTGGCGGATGAG-3' (SEQ ID NO: 19) | 5'-CAGCAGCTTGCAGTGTGGAC-3' (SEQ ID NO: 20) |
| pyruvate dehydrogenase kinase-4 (Pdk4) | 5'-TCCTGCCTGACCGCTTAGTG-3' (SEQ ID NO: 21) | 5t-GCGTGTCTACAAACTCTGACAGG-3' (SEQ ID NO: 22) |
| uncoupling protein-3 (UCP3) | 5'-CCCGGTGGATGTGGTAATGAC-3' (SEQ ID NO: 23) | 5'-CAAGCTCCCAGACGCAGAAAG-3' (SEQ ID NO: 24) |
| myosin heavy chain polypeptide 4 (Myh4) | 5'-CTTCATCTGGTAACACAAGAGGTGC-3' (SEQ ID NO: 25) | 5'-TTCTGGGCCTCGATTCGCTC-3' (SEQ ID NO: 26) |
| myosin heavy chain polypeptide 1 (Myh1) | 5'-CCCTAAAGGCAGGCTCTCTCA-3' (SEQ ID NO: 27) | 5t-TCCCCGAAAACGGCCATCTC-3' (SEQ ID NO: 28) |
| myosin heavy chain polypeptide 2 (Myh2) | 5'-AAGAGTCCCGAACGAGGCTG-3' (SEQ ID NO: 29) | 5'-ACTCACAGACCCTTACTGGCA-3' (SEQ ID NO: 30) |

(Immunoblotting)

Total protein lysates were obtained from muscle tissues after exposure to RIPA buffer (Thermo Fisher Scientific, Yokohama, Japan). Primary antibodies were diluted in CanGetSignal (registered trade mark) solution A (Toyobo) and incubated at 4° C. overnight. Then, horseradish peroxidase (HRP)-labeled secondary antibodies were diluted in CanGetSignal (registered trade mark) solution B (Toyobo) and incubated at room temperature for 1 h. HRP-labeled secondary antibodies were visualized by chemiluminescence with a digital luminescent image analyzer LAS-4000 (GE Healthcare, Tokyo, Japan).

(Immunostaining)

Immunohistochemistry was performed on muscle tissue according to a previous report (Ono, Y., Calhabeu, F., Morgan, J. E., Katagiri, T., Amthor, H., and Zammit, P. S. (2011) Cell Death Differ 18, 222-234). Frozen muscle cross sections were fixed with 4% paraformaldehyde, blocked with an M.O.M. kit (Vector Laboratories), and incubated with primary antibodies at 4° C. overnight. All immunostaining samples were visualized by using appropriate species-specific Alexa Fluor 488 and/or 568 fluorescence-labeled secondary antibodies (Life Technologies). Samples were then viewed on the Olympus IX83 microscope (Olympus, Tokyo, Japan). Digital images were acquired and quantified with a DP80 camera and cellSens software (Olympus). Images were optimized globally and assembled into figures with Adobe Photoshop.

(Statistical Analysis)

Significant differences were determined with Student's t test. $P<0.05$ was regarded as statistically significant. All data show mean±standard error of the mean (SEM).

Results

High Expression of Crym in Skeletal Muscle of Adult Mice

To examine expression profile of Crym gene throughout the body, wild-type (WT) mouse tissues were analyzed by Q-PCR. As already reported (Kim, R. Y., Gasser, R., and Wistow, G. J. (1992) Proceedings of the National Academy of Sciences of the United States of America 89, 9292-9296), Crym was highly expressed in the brain and kidney and selectively expressed in the skeletal muscle (FIG. 1A). FSHD affects specific muscle regions, particularly on the proximal muscle of the forelimbs (Lek, A., Rahimov, F., Jones, P. L., and Kunkel, L. M. (2015) Trends in molecular medicine 21, 295-306, Ciciliot, S., Rossi, A. C., Dyar, K. A., Blaauw, B., and Schiaffino, S. (2013) The international journal of biochemistry & cell biology 45, 2191-2199). Abnormal expression of Crym was not observed in the triceps brachii muscle and tibialis anterior (TA) muscle, which are preferentially affected in patients with FSHD (Tawil, R., van der Maarel, S. M., and Tapscott, S. J. (2014) Skeletal muscle 4, 12) (FIG. 1A).

To explore further the expression pattern of Crym during myogenic progression in vitro, satellite cells, which are stem cells internally present in the tissue of skeletal muscle, were analyzed by Q-PCR. The Q-PCR data showed that the expression of Crym was highly up-regulated during myogenic differentiation induced by serum-reduced medium (DM) for 3 d, compared with proliferative myoblasts maintained in mitogen-rich medium (GM) (FIG. 1B).

Crym−/− Mice Showed Increase in Muscle Force and High Running Ability

Since expression of Crym was clear in the muscle tissue in vivo, physiological function of Crym in the skeletal muscle was then examined using Crym-knockout mice (Suzuki, S., Suzuki, N., Mori, J., Oshima, A., Usami, S., and Hashizume, K. (2007) Mol Endocrinol 21, 885-894).

Figure 2:
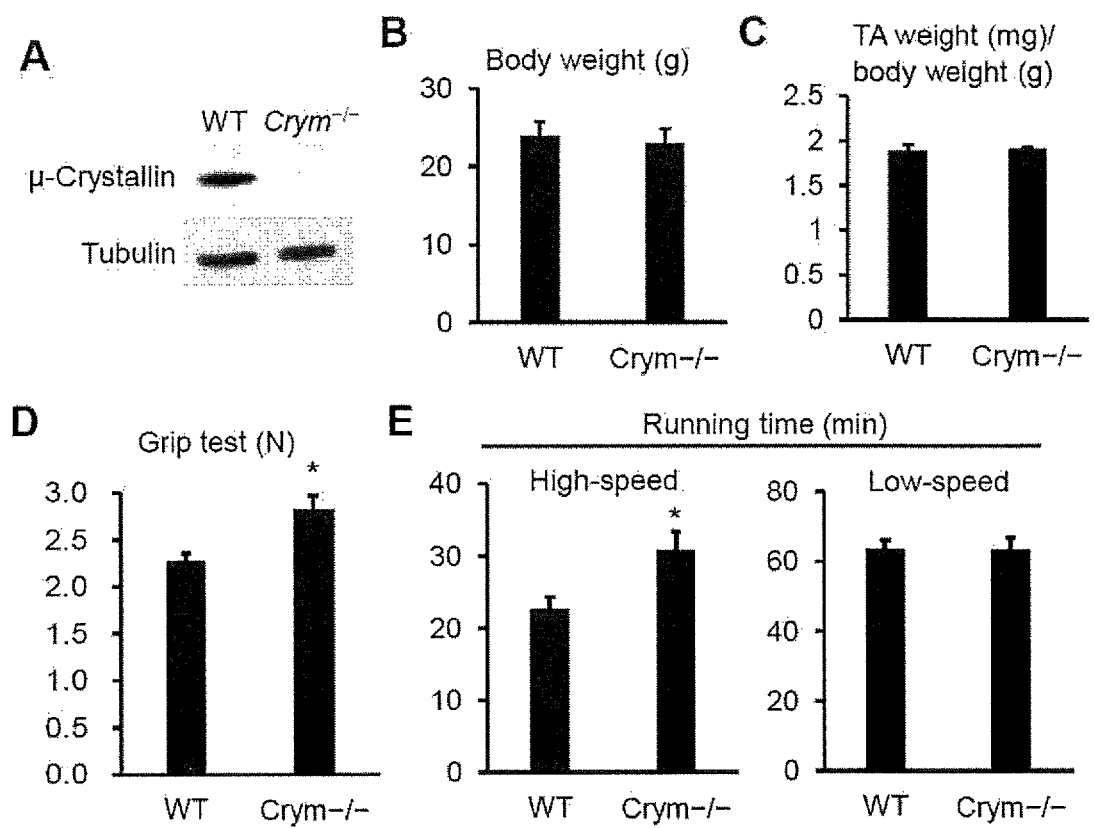
FIG. 2 shows increased muscle force and high-speed running ability of Crym-deficient mice. (A) Immunoblot analysis for Crym protein in TA muscles of WT and Crym−/− mice. Tubulin was used as an internal control. (B) Similar to published report (Suzuki, S., Suzuki, N., Mori, J., Oshima, A., Usami, S., and Hashizume, K. (2007) Mol Endocrinol 21, 885-89412), no obvious deleterious effect was observed for the total body weight of Crym−/− mice (WT, n=6; KO, n=6). (C) Muscle weight was measured in Crym−/− mice (WT, n=6; KO, n=6). (D) Grip test to measure muscle force generation was evaluated in Crym−/− mice (WT, n=10; KO, n=10; 6-8 wk old). (E) The results of a treadmill running test to measure endurance exercise abilities at high speed (velocity increased 5 m/min every 2 min) (WT, n=10; KO, n=8) and low speed (velocity increased 1 m/min every 3 min) (WT, n=6; KO, n=6) are shown. The data is shown in mean±SEM; *p<0.05, a significant difference is based on the comparison with WT mice.

Immunoblot analysis confirmed that Crym protein in TA muscle was detectable in WT mice but undetectable in Crym-deficient mice (FIG. 2A). In agreement with previous study (Suzuki, S., Suzuki, N., Mori, J., Oshima, A., Usami, S., and Hashizume, K. (2007) Mol Endocrinol 21, 885-894), it was also found that homozygous deletion of Crym (Crym−/−) does not cause obvious deleterious development or growth in mice (data not shown). There was no difference in body and muscle weight between WT and Crym−/− mice (FIG. 2B, C). Also, it was confirmed that the weights of other tissues including liver, white adipose tissue, heart, kidney and brain do not show a significant difference (data not shown). Interestingly, the grip test analysis revealed that limb muscle force generation was up-regulated in Crym−/− mice (FIG. 2D). Crym−/− mice displayed correspondingly fatigue resistance in a high-speed running test, but not in a low-speed endurance running test (FIG. 2E). These results suggest that the inactivation of Crym increases maximum muscle contraction and high-speed running performance in mice.

Inactivation of Crym Promotes Fast-Twitch Glycolytic Muscle Formation

Figure 3:
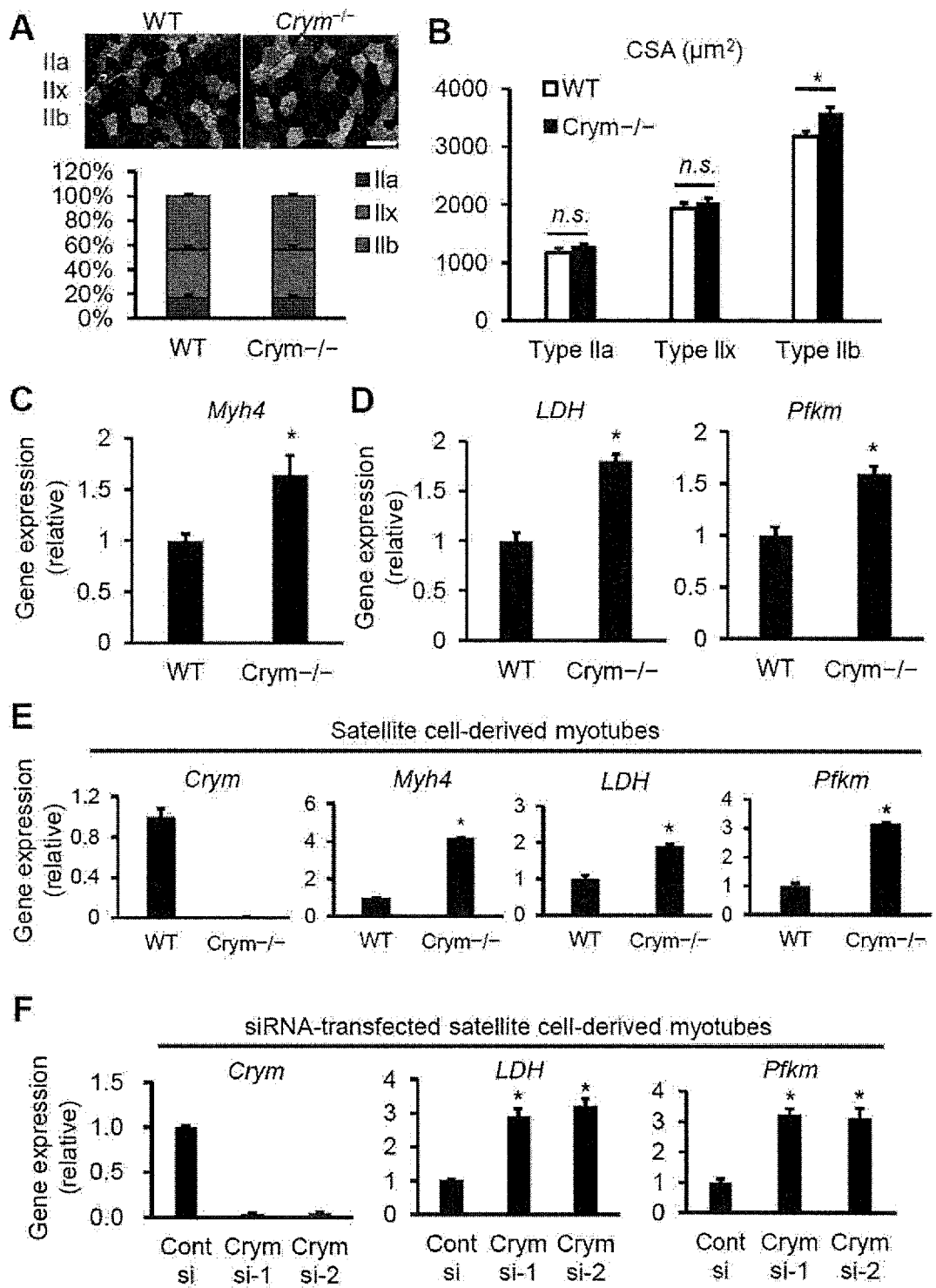
FIG. 3 shows Crym inactivation results in hypertrophy of type IIb myofiber. Effects of Crym inactivation on muscle properties. (A) Immunohistochemical analysis of the proportion of fiber-type composition (WT, n=4; KO, n=4). (B) Individual fiber type sectional area (CSA) in TA muscle derived from Crym−/− mice (WT, n=6; KO, n=6). (C) Q-PCR analysis of the expression of Myh4 (corresponding to type IIb fiber) genes in TA muscle (WT, n=6; KO, n=6). (D) Q-PCR analysis revealed the expression profile of glycolytic enzymes (LDH and Pfkm) in Crym-deficient mice (WT, n=3; KO, n=3). (E, F) Satellite cells were isolated from EDL muscle as described in FIG. 1. Gene expression profiles for glycolytic enzymes in Crym−/− satellite cell derived myotubes (E) (WT, n=3; KO, n=3) and myotubes transfected with targeting siRNA against Crym (F) (Cont si, n=3; Crym si, n=3). The data is shown in mean±SEM; *p<0.05, a significant difference is based on the comparison with WT or control mice; Scale bar: 100 μm.

The muscle strength was up-regulated in Crym−/− mice. Then, the properties of the skeletal muscle of Crym−/− mice were evaluated. The immunohistochemistry reveals that the cross-sectional area (CSA) of type II b fiber of TA muscles significantly increased in Crym−/− mice as compared with that of WT mice, though the proportion of the fiber-type composition did not change (FIG. 3A, B). In agreement with the immunohistochemistry analysis, the expression of type II b (Myh4) gene was up-regulated in TA muscles derived from Crym−/− mice (FIG. 3C).

To determine fiber-type properties, the metabolic profile of Crym−/− muscles was evaluated. Q-PCR analysis revealed that glycolytic enzyme [lactate dehydrogenase A (LDH) and muscle type phosphofructokinase (Pfkm)] genes were highly expressed in Crym−/− skeletal muscle (FIG. 3D). Then, whether these changes can be observed in satellite cell-derived myotubes was tested in vitro. Satellite cells play a crucial role in providing myonuclei for postnatal muscle growth and for maintenance, repair/regeneration, and hypertrophy in adults (Relaix, F., and Zammit, P. S. (2012) Development 139, 2845-2856, Blau, H. M., Cosgrove, B. D., and Ho, A. T. (2015) Nature medicine 21, 854-862). According to previous reports, Satellite cells isolated from EDL were cultured and induced to differentiate and form myotubes by DM (Masuda, S., Hisamatsu, T., Seko, D., Urata, Y., Goto, S., Li, T. S., and Ono, Y. (2015) Physiological reports 3). It was observed that WT mice and Crym−/− mice are not different in the proliferation and myogenic abilities (data not shown). The Q-PCR analysis showed that glycolytic enzymes also increased in both Crym−/− myotubes (FIG. 3E) and myotubes transfected with siRNA against Crym (FIG. 3F).

Figure 4:
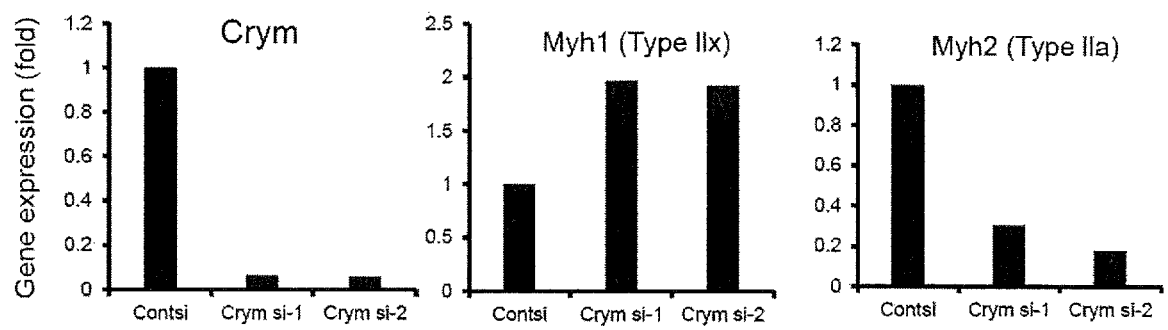
FIG. 4 shows the effect of Crym knockdown on the expression of type IIx (Myh1) gene and type IIa (Myh2) gene. Gene expression of Myh1 and Myh2 in myotube transfected with targeting siRNA against Crym is shown (Cont si, n=1; Crym si, n=1).

Similarly, siRNA against Crym was transfected to satellite cell-derived myotubes, and expression of type IIx (Myh1) gene and type IIa (Myh2) gene was tested in vitro. By Q-PCR analysis, Myh1 increased but Myh2 decreased, from which conversion to fast muscle is considered to have been induced (FIG. 4).

Thyroid Hormone-Responsive Genes are Up-Regulated in Crym−/− Muscle

Thyroid hormones potently induce the expression of genes for conversion to glycolytic fast fiber-type in muscle (Salvatore, D., Simonides, W. S., Dentice, M., Zavacki, A. M., and Larsen, P. R. (2014) Nature reviews. Endocrinology 10, 206-214; Clement, K., Viguerie, N., Diehn, M., Alizadeh, A., Barbe, P., Thalamas, C., Storey, J. D., Brown, P. O., Barsh, G. S., and Langin, D. (2002) Genome research 12, 281-291; Nwoye, L., Mommaerts, W. F., Simpson, D. R., Seraydarian, K., and Marusich, M. (1982) The American journal of physiology 242, R401-408; Bahi, L., Garnier, A., Fortin, D., Serrurier, B., Veksler, V., Bigard, A. X., and Ventura-Clapier, R. (2005) J Cell Physiol 203, 589-598). Having shown that Crym−/− muscles displayed a higher expression of genes for fast-twitch glycolytic fibers compared with that of WT mouse muscles, whether inactivation of Crym affects the thyroid hormone status in skeletal muscle was determined. Uncoupling protein-3 (UCP3) is a target gene of thyroid hormone and its expression level is regulated by a thyroid hormone response element in the proximal promoter region in muscles (Solanes, G., Pedraza, N., Calvo, V., Vidal-Puig, A., Lowell, B. B., and Villarroya, F. (2005) The Biochemical journal 386, 505-513; Gong, D. W., He, Y., Karas, M., and Reitman, M. (1997) The Journal of biological chemistry 272, 24129-24132).

Figure 5:
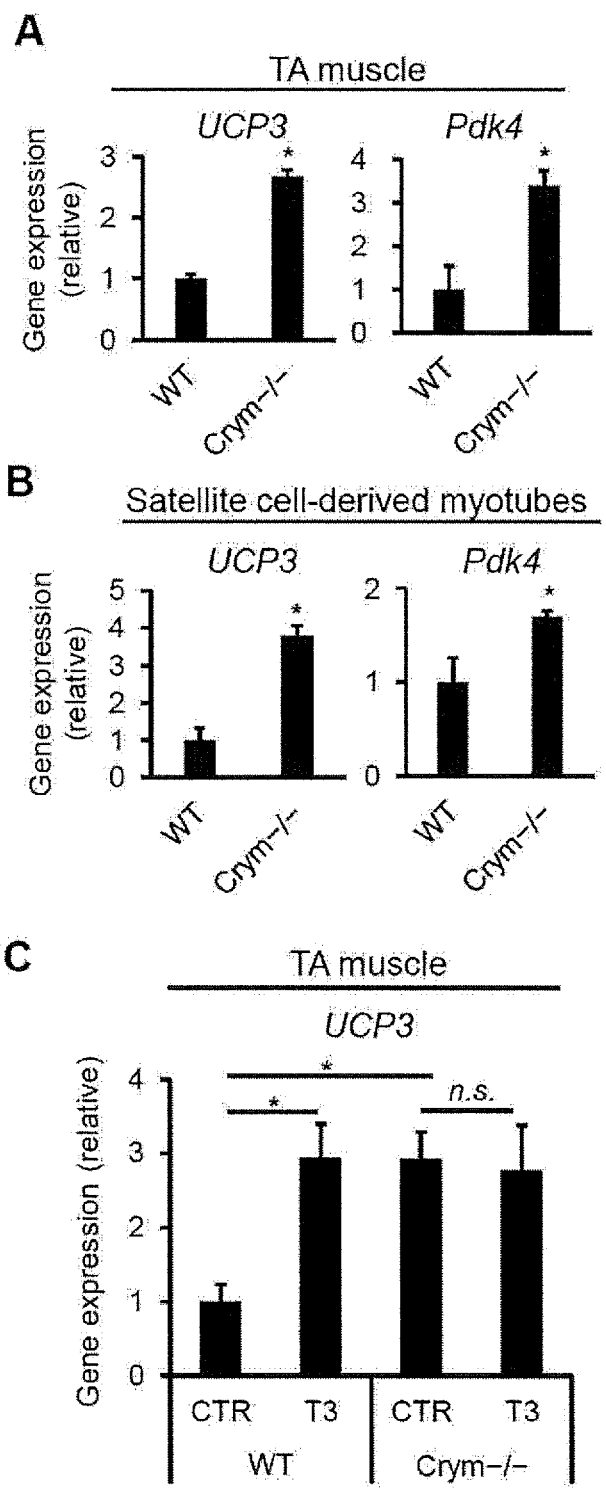
FIG. 5 shows that thyroid hormone-responsive genes are increased in Crym−/− muscle. (A, B) Q-PCR analysis for thyroid hormone-responsive genes (UCP3 and Pdk4) in Crym−/− muscle. Gene expression of UCP3 and Pdk4 in (A) TA muscle of Crym−/− mice (WT, n=6; KO, n=6) and (B) Crym−/− satellite cell-derived myotubes (WT, n=3; KO, n=3). (C) To increase thyroid hormone action, T3 was administered to Crym−/− mice for 2 wk. Q-PCR analysis showed the gene expression of UCP3 in TA muscle (WT, n=3; KO, n=3). The data is shown in mean±SEM; *p<0.05, a significant difference is based on the comparison with WT mice.

Pyruvate dehydrogenase kinase-4 (Pdk4) is a major target gene of T3 (Orfali, K. A., Fryer, L. G., Holness, M. J., and Sugden, M. C. (1995) Journal of molecular and cellular cardiology 27002C901-908). It was shown that the expression of UCP3 and Pdk4 was up-regulated in muscle tissues and satellite cell-derived Crym−/− myotubes (FIG. 5A, B).

To evaluate further the effect of hyperthyroidism on Crym−/− muscle, the hyperthyroid status was induced by feeding drinking water containing T3 (5 µg/ml) for 2 weeks. Treatment with T3 led to the up-regulation of UCP3 expression in WT muscle, but not in Crym−/− muscle (FIG. 5C). These results indicate that thyroid hormone action is maximally amplified in Crym−/− muscle in the euthyroid state.

Figure 6:
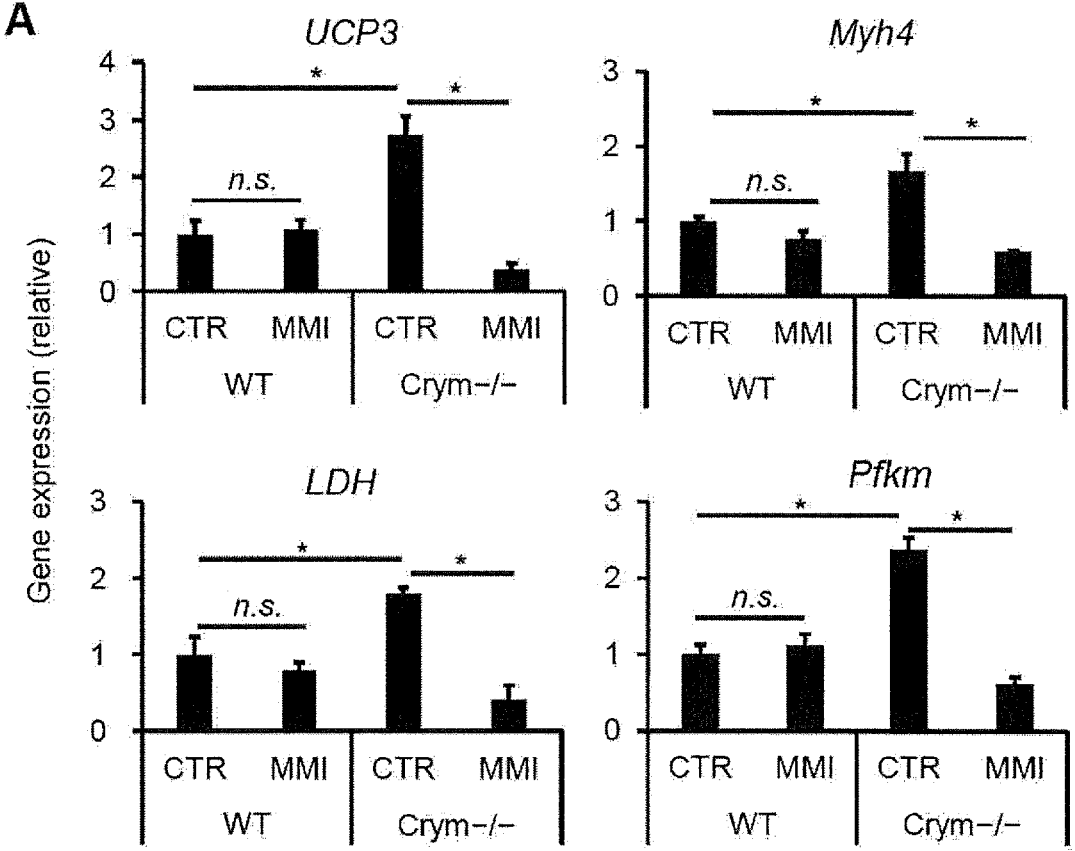
FIG. 6 shows inhibition of thyroid hormone rescues the phenotypes of Crym−/− muscle. Hypothyroidism was induced by providing drinking water containing MMI, an inhibitor of thyroid hormone synthase for 21 d. (A) Gene expression profile of thyroid hormone target genes (WT, n=4; KO, n=4). (B) Immunohistochemical analysis of CSA of individual fiber types in TA muscle of Crym−/− mice (WT, n=5; KO, n=5). (C, D) Grip test and a high-speed running test were performed as shown in FIG. 2. (C) Grip test to measure muscle force generation in Crym−/− mice (WT, n=10; KO, n=7; 13 wk old). (D) Treadmill running test to measure endurance exercise abilities at high-speed, as described in FIG. 2 (WT, n=9; KO, n=5). The data is shown in mean±SEM; *p<0.05, a significant difference is based on the comparison with WT mice.
Figure 6:
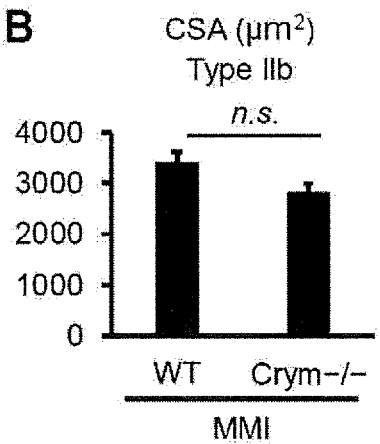
Figure 6:
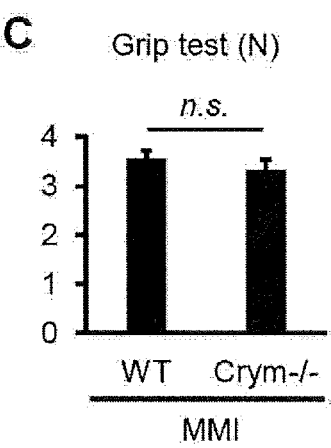
Figure 6:
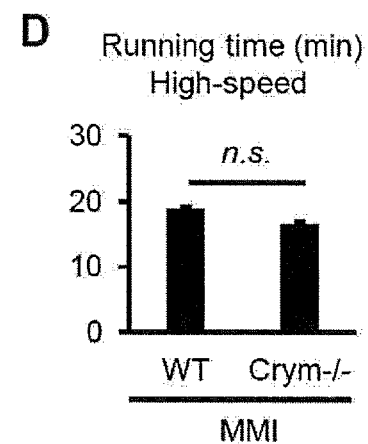

Thyroid Hormone Synthesis Inhibitory Rescues Phenotypes in Crym-Deficient Muscle Whether a treatment with a thyroid hormone inhibitor rescues an effect on in vivo Crym-inactivated muscle was examined. Inhibition of thyroid hormone synthesis was induced by having mice drink drinking water containing 0.1% MMI, a potent inhibitor of thyroid hormone synthase thyroperoxidase for 21 d. Disruption of thyroid hormone synthase resulted in a significant reduction in the expression of thyroid hormone-responsive genes in Crym−/− muscle, whereas WT mice were unaffected (FIG. 6A). Importantly, inhibition of thyroid hormone synthesis sufficiently rescued all phenotypes of increased type IIb hypertrophy (FIG. 6B), grip strength (FIG. 6C) and high-speed running performance (FIG. 6D) in Crym−/− mice. Taken together, these results suggest that a Crym deficit promotes glycolytic fast fiber-type formation by enhancing thyroid hormone action in muscles.

DISCUSSION

Crym is expressed in the ocular lens of marsupials and other tissues, including brain, kidney, and skeletal muscle (Kim, R. Y., Gasser, R., and Wistow, G. J. (1992) Proceedings of the National Academy of Sciences of the United States of America 89, 9292-9296). Up-regulation of Crym expression has also been reported in FSHD-affected muscles (Reed, P. W., Corse, A. M., Porter, N. C., Flanigan, K. M., and Bloch, R. J. (2007) Experimental neurology 205, 583-586; Vanderplanck, C., Ansseau, E., Charron, S., Stricwant, N., Tassin, A., Laoudj-Chenivesse, D., Wilton, S. D., Coppee, F., and Belayew, A. (2011) PloS one 6, e26820). Recent studies revealed that Crym functions as a thyroid hormone-binding protein, however, the physiological role of Crym in muscle remains unknown. It was shown that the Crym gene was highly expressed in skeletal muscle, but was expressed at a low level in other metabolic organs, such as liver and adipose tissues. This suggests that Crym is not a universal regulator of thyroid hormone signaling throughout the body. Gene expression analysis also revealed that abnormal expression of Crym was not observed in the preferentially affected muscles of patients with FSHD (including the triceps and TA muscles) (Tawil, R., van der Maarel, S. M., and Tapscott, S. J. (2014) Skeletal muscle 4, 12).

There is a preferential association of fast-type fibers with the pathological dystrophic process in muscular diseases. Previous studies reported loss of specific force in the fastest type IIb fiber in dystrophic mouse models (Sampaolesi, M., Torrente, Y., Innocenzi, A., Tonlorenzi, R., D'Antona, G., Pellegrino, M. A., Barresi, R., Bresolin, N., De Angelis, M. G., Campbell, K. P., Bottinelli, R., and Cossu, G. (2003) Science 301, 487-492; Denti, M. A., Rosa, A., D'Antona, G., Sthandier, O., De Angelis, F. G., Nicoletti, C., Allocca, M., Pansarasa, O., Parente, V., Musaro, A., Auricchio, A., Bottinelli, R., and Bozzoni, I. (2006) Proceedings of the National Academy of Sciences of the United States of America 103, 3758-3763). Patients with FSHD exhibit a reduction of force generation of type II muscle and a conversion from fast glycolytic to slow oxidative fibers (Celegato, B., Capitanio, D., Pescatori, M., Romualdi, C., Pacchioni, B., Cagnin, S., Vigano, A., Colantoni, L., Begum, S., Ricci, E., Wait, R., Lanfranchi, G., and Gelfi, C. (2006) Proteomics 6, 5303-5321). A recent study has revealed that type II muscle fibers in patients with FSHD produce significantly less force, compared with those of healthy controls (Lassche, S., Stienen, G. J., Irving, T. C., van der Maarel, S. M., Voermans, N. C., Padberg, G. W., Granzier, H., van Engelen, B. G., and Ottenheijm, C. A. (2013) Neurology 80, 733-737). It is suggested that the hypoactivity of type II fibers plays a role in the development of muscle weakness in FSHD.

The present inventor has found that Crym-deficient mouse shows a significant hypertrophy of fast glycolytic fibers. Thus, increased Crym expression may be involved in the development of FSHD pathology. However, the present inventor did not evaluate the effect of Crym gain-of-function on the muscle function. Further studies are needed to elucidate how overexpressed Crym influences muscle properties, to better understand the relationship between Crym expression levels and severity of disease in patients with FSHD.

Thyroid hormone plays important roles in an extensive range of physiological functions throughout the body (Salvatore, D., Simonides, W. S., Dentice, M., Zavacki, A. M., and Larsen, P. R. (2014) Nature reviews. Endocrinology 10, 206-214; Mullur, R., Liu, Y. Y., and Brent, G. A. (2014) Physiological reviews 94, 355-382). Skeletal muscle is a major target of thyroid hormones that are crucial conversion to glycolytic fast fiber-type (Salvatore, D., Simonides, W. S., Dentice, M., Zavacki, A. M., and Larsen, P. R. (2014) Nature reviews. Endocrinology 10, 206-214; Nwoye, L., Mommaerts, W. F., Simpson, D. R., Seraydarian, K., and Marusich, M. (1982) The American journal of physiology 242, R401-408; Bahi, L., Garnier, A., Fortin, D., Serrurier, B., Veksler, V., Bigard, A. X., and Ventura-Clapier, R. (2005) J Cell Physiol 203, 589-598). Previous studies have clarified that Crym regulates transport of T3 from the cytoplasm to the nucleus, and is involved in the control of binding to the thyroid hormone receptor and activation of T3-responsive genes (Suzuki, S., Mori, J., and Hashizume, K. (2007) Trends in endocrinology and metabolism: TEM 18, 286-289). Indeed, Crym is considered a positive regulator of thyroid hormone action (Takeshige, K., Sekido, T., Kitahara, J., Ohkubo, Y., Hiwatashi, D., Ishii, H., Nishio, S., Takeda, T., Komatsu, M., and Suzuki, S. (2014) Endocrine journal 61, 561-570). However, Crym knockout mice exhibit accelerated T3 and thyroxine (T4) turnover in serum and tissues, but normal growth without alterations in peripheral T3 actions (Suzuki, S., Suzuki, N., Mori, J., Oshima, A., Usami, S., and Hashizume, K. (2007) Mol Endocrinol 21, 885-894). The present inventor has shown that inactivation of Crym upregulates thyroid hormone action in the muscle. Importantly, the upregulated thyroid hormone signaling in Crym-inactivated muscle was rescued by inhibiting the production of thyroid hormone.

These findings mean that Crym functions as a negative regulator of thyroid hormone action in skeletal muscle. Therefore, it is assumed that reduced Crym translocates T3 into the nucleus and T3 is bonded to a thyroid hormone receptor to promote expression of the thyroid hormone-responsive genes. It is important to take note of the fact that an inhibitory effect on the thyroid hormone synthesis could not be exhibited on the expression of thyroid hormone target genes in the muscle of wild-type mouse. These phenomena may be explained by previous findings that cells normally store T4 and T3 in the cytoplasm and that anti-thyroid drug-induced hypothyroidism up-regulates the activity of type 2 iodothyronine selenodeiodinases (Dio2), which converts T4 to T3, in skeletal muscle (Marsili, A., Ramadan, W., Harney, J. W., Mulcahey, M., Castroneves, L. A., Goemann, I. M., Wajner, S. M., Huang, S. A., Zavacki, A. M., Maia, A. L., Dentice, M., Salvatore, D., Silva, J. E., and Larsen, P. R. (2010) Endocrinology 151, 5952-5960; Dentice, M., Ambrosio, R., Damiano, V., Sibilio, A., Luongo, C., Guardiola, O., Yennek, S., Zordan, P., Minchiotti, G., Colao, A., Marsili, A., Brunelli, S., Del Vecchio, L., Larsen, P. R., Tajbakhsh, S., and Salvatore, D. (2014) Cell metabolism 20, 1038-1048).

In conclusion, the effects of inactivation of Crym on the properties of skeletal muscle were investigated. Although Crym mediates thyroid hormone signaling in nonmuscle cells, it appears to act as a negative regulator for T3 action in muscles. These findings suggest that Crym regulates thyroid hormone status in a cell- and tissue-specific manner. Taken together, Crym is an extremely important regulator of muscle plasticity, regulating metabolic and contractile phenotypes, at least in part, by regulating thyroid hormone action in skeletal muscle.

Selectively targeting Crym may be a potential therapeutic option for FSHD and also for age-related sarcopenia, which involves significant muscle atrophy, especially in the type II fibers. Recent studies reported that Crym also functions as a ketimine reductase (Hallen, A., Cooper, A. J., Jamie, J. F., Haynes, P. A., and Willows, R. D. (2011) Journal of neurochemistry 118, 379-387; Borel, F., Hachi, I., Palencia, A., Gaillard, M. C., and Ferrer, J. L. (2014) The FEBS journal 281, 1598-1612). Therefore, it remains unclear whether it also regulates muscle plasticity in a thyroid hormone-independent manner. Further studies are needed to uncover the physiological and pathological functions of Crym.

INDUSTRIAL APPLICABILITY

The therapeutic agent for a muscle weakness symptom or a metabolic disease of the present invention enhances muscle force of the skeletal muscle and improves metabolism, and is particularly useful for the treatment of sarcopenia and a disorder of carbohydrate metabolism.

This application is based on a patent application No. 2015-179698 filed in Japan (filing date: Sep. 11, 2015), the contents of which are incorporated in full herein.

---

The invention claimed is:

1. A method for treating sarcopenia, comprising administering an effective amount of a CRYM inhibitory substance to a subject in need thereof, wherein the CRYM inhibitory substance is selected from the group consisting of an antisense nucleic acid against CRYM, an RNAi-inducing nucleic acid against CRYM, a ribozyme against CRYM, expression vectors of any of the foregoing, and an antagonist antibody against CRYM.

2. The treatment method according to claim 1, wherein the subject has sarcopenia, wherein the sarcopenia is selected from the group consisting of primary sarcopenia, activity-related sarcopenia, disease-related sarcopenia and nutrition-related sarcopenia, and wherein the sarcopenia is associated with a metabolic disease.

3. The treatment method according to claim 2, wherein the metabolic disease is a disorder of carbohydrate metabolism or a disorder of lipid metabolism.

4. The treatment method according to claim 3, wherein the CRYM inhibitory substance is an antisense nucleic acid against CRYM or an expression vector thereof.

5. The treatment method according to claim 3, wherein the CRYM inhibitory substance is an RNAi-inducing nucleic acid against CRYM or an expression vector thereof.

6. The treatment method according to claim 3, wherein the CRYM inhibitory substance is a ribozyme against CRYM or an expression vector thereof.

7. The treatment method according to claim 3, wherein the CRYM inhibitory substance is an antagonist antibody against CRYM.

8. The treatment method according to claim 1, wherein the CRYM inhibitory substance is an antisense nucleic acid against CRYM or an expression vector thereof.

9. The treatment method according to claim 1, wherein the CRYM inhibitory substance is an RNAi-inducing nucleic acid against CRYM or an expression vector thereof.

10. The treatment method according to claim 1, wherein the CRYM inhibitory substance is a ribozyme against CRYM or an expression vector thereof.

11. The treatment method according to claim 1, wherein the CRYM inhibitory substance is an antagonist antibody against CRYM.

* * * * *

SEQUENCE LISTING

```
<160> NUMBER OF SEQ ID NOS: 30

<210> SEQ ID NO 1
<211> LENGTH: 1559
<212> TYPE: DNA
<213> ORGANISM: Homo sapiens
<220> FEATURE:
<221> NAME/KEY: CDS
<222> LOCATION: (352)..(1296)

<400> SEQUENCE: 1
ttgttcccgt gctcttctca tgatagtgag taagtctcat aagaactgat ggttttcaaa      60
tggggagttt ccctgcacaa gctttcttgt ctgccactat gtgagatata cctttcacct     120
tctgccgtga ttgtgaggcc tcctcagcca cgtggaactg taaaaactcc tggaagaaaa     180
gatcctgcaa tttggctttt tgtgagatgg aaaagattac accttgccct gcaaacttcc     240
cccctttaaa ggcgaaggtt tgttagagca gcgggcgcgc tcataaaggg cacagccgag     300
ggtacgtgga tcgcggtgcg gagactgagg ttagaaggca caggtggcga g atg agc     357
                                                         Met Ser
                                                           1 cgg gta cca gcg ttc ctg agc gcg gcc gag gtg gag gaa cac ctc cgc      405
Arg Val Pro Ala Phe Leu Ser Ala Ala Glu Val Glu Glu His Leu Arg
        5                   10                  15 agc tcc agc ctc ctc atc ccg cct cta gag acg gcc ctg gcc aac ttc      453
Ser Ser Ser Leu Leu Ile Pro Pro Leu Glu Thr Ala Leu Ala Asn Phe
     20                  25                  30 tcc agc ggt ccc gaa gga ggg gtc atg cag ccc gtg cgc acc gtg gtg      501
Ser Ser Gly Pro Glu Gly Gly Val Met Gln Pro Val Arg Thr Val Val
 35                  40                  45                  50 ccg gtg acc aag cac agg ggc tac ctg ggg gtc atg ccc gcc tac agt      549
Pro Val Thr Lys His Arg Gly Tyr Leu Gly Val Met Pro Ala Tyr Ser
                 55                  60                  65 gct gca gag gat gca ctg acc acc aag ttg gtc acc ttc tac gag gac      597
Ala Ala Glu Asp Ala Leu Thr Thr Lys Leu Val Thr Phe Tyr Glu Asp
             70                  75                  80
```

| | | | | | | | | | | | | | | | |
|---|---|---|---|---|---|---|---|---|---|---|---|---|---|---|---|
| cgc | ggc | atc | acc | tcg | gtc | gtc | cct | tcc | cac | cag | gct | act | gtg | cta | ctc | 645 |
| Arg | Gly | Ile | Thr | Ser | Val | Val | Pro | Ser | His | Gln | Ala | Thr | Val | Leu | Leu | |
| | | 85 | | | | | 90 | | | | | 95 | | | | |
| ttt | gag | ccc | agc | aat | ggc | acc | ctg | ctg | gcg | gtc | atg | gat | gga | aat | gtc | 693 |
| Phe | Glu | Pro | Ser | Asn | Gly | Thr | Leu | Leu | Ala | Val | Met | Asp | Gly | Asn | Val | |
| 100 | | | | | 105 | | | | | 110 | | | | | | |
| ata | act | gca | aag | aga | aca | gct | gca | gtt | tct | gcc | att | gcc | acc | aag | ttt | 741 |
| Ile | Thr | Ala | Lys | Arg | Thr | Ala | Ala | Val | Ser | Ala | Ile | Ala | Thr | Lys | Phe | |
| 115 | | | | | 120 | | | | | 125 | | | | | 130 | |
| ctg | aaa | cct | ccc | agc | agt | gaa | gtg | ctg | tgc | atc | ctt | ggg | gct | ggg | gtc | 789 |
| Leu | Lys | Pro | Pro | Ser | Ser | Glu | Val | Leu | Cys | Ile | Leu | Gly | Ala | Gly | Val | |
| | | | | | 135 | | | | | 140 | | | | | 145 | |
| cag | gcc | tac | agc | cat | tat | gag | atc | ttc | aca | gag | cag | ttc | tcc | ttt | aag | 837 |
| Gln | Ala | Tyr | Ser | His | Tyr | Glu | Ile | Phe | Thr | Glu | Gln | Phe | Ser | Phe | Lys | |
| | | | | 150 | | | | | 155 | | | | | 160 | | |
| gag | gtg | agg | ata | tgg | aac | cgc | acc | aaa | gaa | aat | gca | gag | aag | ttt | gca | 885 |
| Glu | Val | Arg | Ile | Trp | Asn | Arg | Thr | Lys | Glu | Asn | Ala | Glu | Lys | Phe | Ala | |
| | | 165 | | | | | 170 | | | | | 175 | | | | |
| gac | aca | gtg | caa | gga | gag | gta | cgg | gtc | tgt | tct | tcg | gtc | cag | gag | gct | 933 |
| Asp | Thr | Val | Gln | Gly | Glu | Val | Arg | Val | Cys | Ser | Ser | Val | Gln | Glu | Ala | |
| | 180 | | | | | 185 | | | | | 190 | | | | | |
| gtg | gca | ggt | gca | gat | gtg | atc | atc | aca | gtc | acc | ctg | gca | aca | gag | ccc | 981 |
| Val | Ala | Gly | Ala | Asp | Val | Ile | Ile | Thr | Val | Thr | Leu | Ala | Thr | Glu | Pro | |
| 195 | | | | | 200 | | | | | 205 | | | | | 210 | |
| att | ttg | ttt | ggt | gaa | tgg | gtg | aag | cca | ggg | gct | cac | atc | aat | gct | gtt | 1029 |
| Ile | Leu | Phe | Gly | Glu | Trp | Val | Lys | Pro | Gly | Ala | His | Ile | Asn | Ala | Val | |
| | | | | 215 | | | | | 220 | | | | | 225 | | |
| gga | gcc | agc | aga | cct | gac | tgg | aga | gaa | ctg | gat | gat | gag | ctc | atg | aaa | 1077 |
| Gly | Ala | Ser | Arg | Pro | Asp | Trp | Arg | Glu | Leu | Asp | Asp | Glu | Leu | Met | Lys | |
| | | | 230 | | | | | 235 | | | | | 240 | | | |
| gaa | gct | gtg | ctg | tac | gtg | gat | tcc | cag | gag | gct | gcc | ctg | aag | gag | tct | 1125 |
| Glu | Ala | Val | Leu | Tyr | Val | Asp | Ser | Gln | Glu | Ala | Ala | Leu | Lys | Glu | Ser | |
| | | 245 | | | | | 250 | | | | | 255 | | | | |
| gga | gat | gtc | ctg | ctg | tca | ggg | gcc | gag | atc | ttt | gct | gag | ctg | gga | gaa | 1173 |
| Gly | Asp | Val | Leu | Leu | Ser | Gly | Ala | Glu | Ile | Phe | Ala | Glu | Leu | Gly | Glu | |
| | 260 | | | | | 265 | | | | | 270 | | | | | |
| gtg | att | aag | gga | gtg | aaa | cca | gcc | cac | tgt | gag | aag | acc | acc | gtg | ttc | 1221 |
| Val | Ile | Lys | Gly | Val | Lys | Pro | Ala | His | Cys | Glu | Lys | Thr | Thr | Val | Phe | |
| 275 | | | | | 280 | | | | | 285 | | | | | 290 | |
| aag | tct | ttg | gga | atg | gca | gtg | gaa | gac | aca | gtt | gca | gcc | aaa | ctc | atc | 1269 |
| Lys | Ser | Leu | Gly | Met | Ala | Val | Glu | Asp | Thr | Val | Ala | Ala | Lys | Leu | Ile | |
| | | | | 295 | | | | | 300 | | | | | 305 | | |
| tat | gat | tcc | tgg | tca | tct | ggt | aaa | taa | aacaaggaa | cttgatgttg | | | | | | 1316 |
| Tyr | Asp | Ser | Trp | Ser | Ser | Gly | Lys | | | | | | | | | |
| | | | | 310 | | | | | | | | | | | | | agatggatgc ttgaggaata ttgctgctgg ttctcataat ttctagagta aatgagggag 1376 tccagtcccc agtgaactct cctttttgtgc ttatcatgtt ttaccttaaa tgctgagatc 1436 ctcatttatg tttgtagttg gaaagcaaag ctaggtagcc atttcttctg ttctaccaag 1496 ttataatagc attcatttcc ctttatattt ccctgaaata aagcacattc caattgtgca 1556 gtg 1559

<210> SEQ ID NO 2
<211> LENGTH: 314
<212> TYPE: PRT
<213> ORGANISM: Homo sapiens

<400> SEQUENCE: 2

Met Ser Arg Val Pro Ala Phe Leu Ser Ala Ala Glu Val Glu Glu His

```
              1               5                  10                 15
            Leu Arg Ser Ser Ser Leu Leu Ile Pro Pro Leu Glu Thr Ala Leu Ala
                       20                  25                 30

Asn Phe Ser Ser Gly Pro Glu Gly Val Met Gln Pro Val Arg Thr
                       35                  40                 45

Val Val Pro Val Thr Lys His Arg Gly Tyr Leu Gly Val Met Pro Ala
             50                  55                 60

Tyr Ser Ala Ala Glu Asp Ala Leu Thr Thr Lys Leu Val Thr Phe Tyr
             65                  70                 75                 80

Glu Asp Arg Gly Ile Thr Ser Val Val Pro Ser His Gln Ala Thr Val
                            85                  90                 95

Leu Leu Phe Glu Pro Ser Asn Gly Thr Leu Leu Ala Val Met Asp Gly
                       100                 105                110

Asn Val Ile Thr Ala Lys Arg Thr Ala Ala Val Ser Ala Ile Ala Thr
                       115                 120                125

Lys Phe Leu Lys Pro Pro Ser Ser Glu Val Leu Cys Ile Leu Gly Ala
                       130                 135                140

Gly Val Gln Ala Tyr Ser His Tyr Glu Ile Phe Thr Glu Gln Phe Ser
            145                 150                 155                160

Phe Lys Glu Val Arg Ile Trp Asn Arg Thr Lys Glu Asn Ala Glu Lys
                            165                 170                175

Phe Ala Asp Thr Val Gln Gly Glu Val Arg Val Cys Ser Ser Val Gln
                       180                 185                190

Glu Ala Val Ala Gly Ala Asp Val Ile Ile Thr Val Thr Leu Ala Thr
                       195                 200                205

Glu Pro Ile Leu Phe Gly Glu Trp Val Lys Pro Gly Ala His Ile Asn
            210                 215                 220

Ala Val Gly Ala Ser Arg Pro Asp Trp Arg Glu Leu Asp Asp Glu Leu
            225                 230                 235                240

Met Lys Glu Ala Val Leu Tyr Val Asp Ser Gln Glu Ala Ala Leu Lys
                            245                 250                255

Glu Ser Gly Asp Val Leu Leu Ser Gly Ala Glu Ile Phe Ala Glu Leu
                       260                 265                270

Gly Glu Val Ile Lys Gly Val Lys Pro Ala His Cys Glu Lys Thr Thr
                       275                 280                285

Val Phe Lys Ser Leu Gly Met Ala Val Glu Asp Thr Val Ala Ala Lys
                       290                 295                300

Leu Ile Tyr Asp Ser Trp Ser Ser Gly Lys
            305                 310

<210> SEQ ID NO 3
<211> LENGTH: 1256
<212> TYPE: DNA
<213> ORGANISM: Mus musculus
<220> FEATURE:
<221> NAME/KEY: CDS
<222> LOCATION: (65)..(1006)

<400> SEQUENCE: 3
atttagggct cagctcctgg aacgtggagt gtgtttcagc ccgggttcga aggcaggcgg        60 cgag atg aag cgg gcg cca gcg ttc ctg agc gca gag gag gtg cag gat       109
     Met Lys Arg Ala Pro Ala Phe Leu Ser Ala Glu Glu Val Gln Asp
     1               5                  10                 15 cac ctt cgc agc tcc agc ctt ctc atc cca ccc ctg gag gcc gca ctg       157
His Leu Arg Ser Ser Ser Leu Leu Ile Pro Pro Leu Glu Ala Ala Leu
                20                  25                 30
```

```
gcc aac ttc tcc aaa ggt ccc gac gga ggg gtc atg cag cca gtg cgc     205
Ala Asn Phe Ser Lys Gly Pro Asp Gly Gly Val Met Gln Pro Val Arg
             35                  40                  45 acc gtg gtg cct gta gcc aag cac cga ggc ttc ctg gga gtc atg cct     253
Thr Val Val Pro Val Ala Lys His Arg Gly Phe Leu Gly Val Met Pro
     50                  55                  60 gcc tac agt gct gct gag gat gcg ctc acc acc aag tta gtc acc ttc     301
Ala Tyr Ser Ala Ala Glu Asp Ala Leu Thr Thr Lys Leu Val Thr Phe
 65                  70                  75 tat gag ggc cac agc aac aca gcg gtc ccc tcc cat cag gca tcg gtg     349
Tyr Glu Gly His Ser Asn Thr Ala Val Pro Ser His Gln Ala Ser Val
 80                  85                  90                  95 ctt ctc ttt gat ccc agc aat ggc tcc ctg ctg gcg gtc atg gat gga     397
Leu Leu Phe Asp Pro Ser Asn Gly Ser Leu Leu Ala Val Met Asp Gly
                100                 105                 110 aat gtc ata act gca aag aga aca gca gcg gtg tct gcc att gcc aca     445
Asn Val Ile Thr Ala Lys Arg Thr Ala Ala Val Ser Ala Ile Ala Thr
            115                 120                 125 aag ctg ttg aag ccc cca ggc agt gat gtg ctg tgc atc ctt gga gcg     493
Lys Leu Leu Lys Pro Pro Gly Ser Asp Val Leu Cys Ile Leu Gly Ala
        130                 135                 140 ggg gtc cag gcg tac agt cac tat gag atc ttc aca gag cag ttc tcc     541
Gly Val Gln Ala Tyr Ser His Tyr Glu Ile Phe Thr Glu Gln Phe Ser
    145                 150                 155 ttc aag gag gtg aga atg tgg aac cgc acc agg gaa aat gct gag aag     589
Phe Lys Glu Val Arg Met Trp Asn Arg Thr Arg Glu Asn Ala Glu Lys
160                 165                 170                 175 ttt gca agc aca gtg caa gga gat gtt cgg gtc tgt tca tca gtg cag     637
Phe Ala Ser Thr Val Gln Gly Asp Val Arg Val Cys Ser Ser Val Gln
                180                 185                 190 gag gct gtg aca ggt gct gat gtc atc atc aca gtc acc atg gca aca     685
Glu Ala Val Thr Gly Ala Asp Val Ile Ile Thr Val Thr Met Ala Thr
            195                 200                 205 gag ccc att tta ttt ggt gaa tgg gta aag ccg ggg gct cac atc aat     733
Glu Pro Ile Leu Phe Gly Glu Trp Val Lys Pro Gly Ala His Ile Asn
        210                 215                 220 gct gtt gga gcc agc agg cct gac tgg cga gaa ctg gat gac gag ctc     781
Ala Val Gly Ala Ser Arg Pro Asp Trp Arg Glu Leu Asp Asp Glu Leu
    225                 230                 235 atg agg caa gcg gtg ctg tat gtg gac tcc cgg gag gct gcc ctg aag     829
Met Arg Gln Ala Val Leu Tyr Val Asp Ser Arg Glu Ala Ala Leu Lys
240                 245                 250                 255 gag tca gga gac gtt ctg ttg tca ggg gct gac atc ttt gct gag ctt     877
Glu Ser Gly Asp Val Leu Leu Ser Gly Ala Asp Ile Phe Ala Glu Leu
                260                 265                 270 gga gaa gtg att tca gga gcg aag cct gca cac tgt gag aag acc aca     925
Gly Glu Val Ile Ser Gly Ala Lys Pro Ala His Cys Glu Lys Thr Thr
            275                 280                 285 gtg ttc aaa tct ttg ggg atg gca gtg gaa gac ctg gtt gca gcc aaa     973
Val Phe Lys Ser Leu Gly Met Ala Val Glu Asp Leu Val Ala Ala Lys
        290                 295                 300 tta gta tat gat tct tgg tca tct ggc aag tga gttgaaggaa ccgtgcctga  1026
Leu Val Tyr Asp Ser Trp Ser Ser Gly Lys
    305                 310 gttggccatc acagctcaac actgtttcac aagtgtcaaa atcaaaggag gtccagtccc  1086
cagtgaatgg tagtgattgt cattcataag tactgacacc cctattcatg tttgtggttg  1146
gatagctaaa ccaggtaacc atttcttctg ttaagggtg atggccacat tatctaccct  1206
```
tgatcttact agtcttgtat ctctctgaaa taaatcattt ccacttcttc         1256

<210> SEQ ID NO 4
<211> LENGTH: 313
<212> TYPE: PRT
<213> ORGANISM: Mus musculus

<400> SEQUENCE: 4

Met Lys Arg Ala Pro Ala Phe Leu Ser Ala Glu Glu Val Gln Asp His
1               5                   10                  15

Leu Arg Ser Ser Ser Leu Leu Ile Pro Pro Leu Glu Ala Ala Leu Ala
            20                  25                  30

Asn Phe Ser Lys Gly Pro Asp Gly Gly Val Met Gln Pro Val Arg Thr
        35                  40                  45

Val Val Pro Val Ala Lys His Arg Gly Phe Leu Gly Val Met Pro Ala
    50                  55                  60

Tyr Ser Ala Ala Glu Asp Ala Leu Thr Thr Lys Leu Val Thr Phe Tyr
65                  70                  75                  80

Glu Gly His Ser Asn Thr Ala Val Pro Ser His Gln Ala Ser Val Leu
                85                  90                  95

Leu Phe Asp Pro Ser Asn Gly Ser Leu Leu Ala Val Met Asp Gly Asn
            100                 105                 110

Val Ile Thr Ala Lys Arg Thr Ala Ala Val Ser Ala Ile Ala Thr Lys
        115                 120                 125

Leu Leu Lys Pro Pro Gly Ser Asp Val Leu Cys Ile Leu Gly Ala Gly
    130                 135                 140

Val Gln Ala Tyr Ser His Tyr Glu Ile Phe Thr Glu Gln Phe Ser Phe
145                 150                 155                 160

Lys Glu Val Arg Met Trp Asn Arg Thr Arg Glu Asn Ala Glu Lys Phe
                165                 170                 175

Ala Ser Thr Val Gln Gly Asp Val Arg Val Cys Ser Ser Val Gln Glu
            180                 185                 190

Ala Val Thr Gly Ala Asp Val Ile Ile Thr Val Thr Met Ala Thr Glu
        195                 200                 205

Pro Ile Leu Phe Gly Glu Trp Val Lys Pro Gly Ala His Ile Asn Ala
    210                 215                 220

Val Gly Ala Ser Arg Pro Asp Trp Arg Glu Leu Asp Asp Glu Leu Met
225                 230                 235                 240

Arg Gln Ala Val Leu Tyr Val Asp Ser Arg Glu Ala Ala Leu Lys Glu
                245                 250                 255

Ser Gly Asp Val Leu Leu Ser Gly Ala Asp Ile Phe Ala Glu Leu Gly
            260                 265                 270

Glu Val Ile Ser Gly Ala Lys Pro Ala His Cys Glu Lys Thr Thr Val
        275                 280                 285

Phe Lys Ser Leu Gly Met Ala Val Glu Asp Leu Val Ala Ala Lys Leu
    290                 295                 300

Val Tyr Asp Ser Trp Ser Ser Gly Lys
305                 310

<210> SEQ ID NO 5
<211> LENGTH: 1227
<212> TYPE: DNA
<213> ORGANISM: Rattus norvegicus
<220> FEATURE:
<221> NAME/KEY: CDS
<222> LOCATION: (32)..(973)

```
<400> SEQUENCE: 5
ggcacgagcg ggttcgaagg caggcggcga g atg agg cgg gcg cca gcg ttt        52
                                    Met Arg Arg Ala Pro Ala Phe
                                    1               5 ctg agc gcc gac gag gtg cag gac cac ctc cgc agc tcc agc ctc ctc       100
Leu Ser Ala Asp Glu Val Gln Asp His Leu Arg Ser Ser Ser Leu Leu
            10                  15                  20 atc ccg ccc ctg gag gcc gca ctg gcc aac ttc tcc aaa ggt ccc gac       148
Ile Pro Pro Leu Glu Ala Ala Leu Ala Asn Phe Ser Lys Gly Pro Asp
25                  30                  35 gga ggg gtc atg caa ccg gtg cgc acc gtg gtg cct gtg gcc aag cac       196
Gly Gly Val Met Gln Pro Val Arg Thr Val Val Pro Val Ala Lys His
40                  45                  50                  55 cga ggc ttc ttg gga gtc atg cca gcc tac agt gcc gct gag gat gca       244
Arg Gly Phe Leu Gly Val Met Pro Ala Tyr Ser Ala Ala Glu Asp Ala
                60                  65                  70 ctc acc acc aag tta gtc acc ttc tat gag ggc cac agc aac aat gct       292
Leu Thr Thr Lys Leu Val Thr Phe Tyr Glu Gly His Ser Asn Asn Ala
            75                  80                  85 gtc ccc tcc cac cag gca tca gtg ctt ctc ttt gat ccc agc aat ggt       340
Val Pro Ser His Gln Ala Ser Val Leu Leu Phe Asp Pro Ser Asn Gly
        90                  95                  100 tcc ctg ctg gcg gtc atg gat gga aat gtc ata act gca aag agg aca       388
Ser Leu Leu Ala Val Met Asp Gly Asn Val Ile Thr Ala Lys Arg Thr
105                 110                 115 gca gcc gtc tct gcc atc gcc acc aag ttt ttg aag ccc cca ggc agt       436
Ala Ala Val Ser Ala Ile Ala Thr Lys Phe Leu Lys Pro Pro Gly Ser
120                 125                 130                 135 gat gtg ctg tgc att ctt ggg gct ggg gtc cag gcg tac agt cac tat       484
Asp Val Leu Cys Ile Leu Gly Ala Gly Val Gln Ala Tyr Ser His Tyr
                140                 145                 150 gag atc ttc aca gaa cag ttc tcc ttc aag gag gtg aga atg tgg aac       532
Glu Ile Phe Thr Glu Gln Phe Ser Phe Lys Glu Val Arg Met Trp Asn
            155                 160                 165 cgc acc agg gaa aat gct gag aag ttt gca agc tca gtg caa gga gat       580
Arg Thr Arg Glu Asn Ala Glu Lys Phe Ala Ser Ser Val Gln Gly Asp
        170                 175                 180 gtt cgg gtc tgt tca tca gtg cag gag gct gtg aca ggt gcc gat gtc       628
Val Arg Val Cys Ser Ser Val Gln Glu Ala Val Thr Gly Ala Asp Val
185                 190                 195 atc atc aca gtc acc atg gca acg gag ccc att ttg ttt ggt gaa tgg       676
Ile Ile Thr Val Thr Met Ala Thr Glu Pro Ile Leu Phe Gly Glu Trp
200                 205                 210                 215 gtg aag ccc gga gct cac atc aat gct gtt gga gcc agt aga cct gac       724
Val Lys Pro Gly Ala His Ile Asn Ala Val Gly Ala Ser Arg Pro Asp
                220                 225                 230 tgg cga gaa ctg gat gac gag ctc atg aag caa gca gtg ttg tat gtg       772
Trp Arg Glu Leu Asp Asp Glu Leu Met Lys Gln Ala Val Leu Tyr Val
            235                 240                 245 gac tcc cgg gag gct gcc cta aag gag tca gga gat gtt ctg ttg tca       820
Asp Ser Arg Glu Ala Ala Leu Lys Glu Ser Gly Asp Val Leu Leu Ser
        250                 255                 260 ggg gct gac atc ttt gct gag ctt gga gaa gtg gtt tca gga gcg aag       868
Gly Ala Asp Ile Phe Ala Glu Leu Gly Glu Val Val Ser Gly Ala Lys
265                 270                 275 cct gca tac tgt gag aag acc acg gtg ttc aag tct ttg ggg atg gca       916
Pro Ala Tyr Cys Glu Lys Thr Thr Val Phe Lys Ser Leu Gly Met Ala
280                 285                 290                 295 gtg gag gac ctg gtc gca gcc aaa tta gtg tac gat tcg tgg tca tct       964
Val Glu Asp Leu Val Ala Ala Lys Leu Val Tyr Asp Ser Trp Ser Ser
```

```
Val Glu Asp Leu Val Ala Ala Lys Leu Val Tyr Asp Ser Trp Ser Ser
            300                 305                 310 ggc aag tga gcagaaggag ctgtgcctga gctggatgga cgtcacggct          1013
Gly Lys caaacgctgg ctcagtgtct agatcaaagg aggcctagtc cccagtgaac gggagtgaga 1073 gtcactcata agtattgaca tccctattca tgtttgtggt tggatagcta aaccctttctg 1133 ttaggggggtg atggccacat tacctaccct tgatcttact agccttgtgt gtctctgaaa 1193 taaatcattt ccagttcaaa aaaaaaaaaa aaaa                             1227

<210> SEQ ID NO 6
<211> LENGTH: 313
<212> TYPE: PRT
<213> ORGANISM: Rattus norvegicus

<400> SEQUENCE: 6

Met Arg Arg Ala Pro Ala Phe Leu Ser Ala Asp Glu Val Gln Asp His
1               5                   10                  15

Leu Arg Ser Ser Ser Leu Leu Ile Pro Pro Leu Glu Ala Ala Leu Ala
            20                  25                  30

Asn Phe Ser Lys Gly Pro Asp Gly Gly Val Met Gln Pro Val Arg Thr
        35                  40                  45

Val Val Pro Val Ala Lys His Arg Gly Phe Leu Gly Val Met Pro Ala
50                  55                  60

Tyr Ser Ala Ala Glu Asp Ala Leu Thr Thr Lys Leu Val Thr Phe Tyr
65                  70                  75                  80

Glu Gly His Ser Asn Asn Ala Val Pro Ser His Gln Ala Ser Val Leu
                85                  90                  95

Leu Phe Asp Pro Ser Asn Gly Ser Leu Leu Ala Val Met Asp Gly Asn
            100                 105                 110

Val Ile Thr Ala Lys Arg Thr Ala Ala Val Ser Ala Ile Ala Thr Lys
        115                 120                 125

Phe Leu Lys Pro Pro Gly Ser Asp Val Leu Cys Ile Leu Gly Ala Gly
130                 135                 140

Val Gln Ala Tyr Ser His Tyr Glu Ile Phe Thr Glu Gln Phe Ser Phe
145                 150                 155                 160

Lys Glu Val Arg Met Trp Asn Arg Thr Arg Glu Asn Ala Glu Lys Phe
                165                 170                 175

Ala Ser Ser Val Gln Gly Asp Val Arg Val Cys Ser Ser Val Gln Glu
            180                 185                 190

Ala Val Thr Gly Ala Asp Val Ile Ile Thr Val Thr Met Ala Thr Glu
        195                 200                 205

Pro Ile Leu Phe Gly Glu Trp Val Lys Pro Gly Ala His Ile Asn Ala
210                 215                 220

Val Gly Ala Ser Arg Pro Asp Trp Arg Glu Leu Asp Asp Glu Leu Met
225                 230                 235                 240

Lys Gln Ala Val Leu Tyr Val Asp Ser Arg Glu Ala Ala Leu Lys Glu
                245                 250                 255

Ser Gly Asp Val Leu Leu Ser Gly Ala Asp Ile Phe Ala Glu Leu Gly
            260                 265                 270

Glu Val Val Ser Gly Ala Lys Pro Ala Tyr Cys Glu Lys Thr Thr Val
        275                 280                 285

Phe Lys Ser Leu Gly Met Ala Val Glu Asp Leu Val Ala Ala Lys Leu
290                 295                 300
```

```
Val Tyr Asp Ser Trp Ser Ser Gly Lys
305                 310
```

```
<210> SEQ ID NO 7
<211> LENGTH: 1275
<212> TYPE: DNA
<213> ORGANISM: Macaca mulatta
<220> FEATURE:
<221> NAME/KEY: CDS
<222> LOCATION: (74)..(1018)

<400> SEQUENCE: 7
gcgctcatat agggcacagc cgagggtacg tggatcgcgg tgcggagact gaggttagaa    60
ggcaggtggc gag atg aac cgc gta cca gcg ttc ctg agc gcg gcc gag     109
            Met Asn Arg Val Pro Ala Phe Leu Ser Ala Ala Glu
              1               5                  10 gtg gag gaa cac ctc cgc agc tcc agc ctc ctc atc ccg cct cta gag    157
Val Glu Glu His Leu Arg Ser Ser Ser Leu Leu Ile Pro Pro Leu Glu
         15                  20                  25 acg gcc ctg gcc aac ttc tcc agc ggt ccc gaa gga ggg gtc atg cag    205
Thr Ala Leu Ala Asn Phe Ser Ser Gly Pro Glu Gly Gly Val Met Gln
     30                  35                  40 ccc gtg cgc acc gtg gtg ccg gtg acc aag cac agg ggc tac ctg ggg    253
Pro Val Arg Thr Val Val Pro Val Thr Lys His Arg Gly Tyr Leu Gly
 45                  50                  55                  60 gtc atg ccc gcc tac agt gct gca gag gat gcc ctg acc acc aag ttg    301
Val Met Pro Ala Tyr Ser Ala Ala Glu Asp Ala Leu Thr Thr Lys Leu
                 65                  70                  75 gtc acc ttc tac gag gac cgc ggc atc acc tca gtc gtc ccc tcc cac    349
Val Thr Phe Tyr Glu Asp Arg Gly Ile Thr Ser Val Val Pro Ser His
                 80                  85                  90 cag gct act gtg cta ctc ttt gag ccc agc aat ggc acc ctg ctg gcg    397
Gln Ala Thr Val Leu Leu Phe Glu Pro Ser Asn Gly Thr Leu Leu Ala
             95                 100                 105 gtc atg gat gga aat gtc ata act gca aag aga aca gct gcg gtt tct    445
Val Met Asp Gly Asn Val Ile Thr Ala Lys Arg Thr Ala Ala Val Ser
    110                 115                 120 gcc att gcc acc aag ttt ctg aaa ccc ccc agc agt gaa gtg ctg tgc    493
Ala Ile Ala Thr Lys Phe Leu Lys Pro Pro Ser Ser Glu Val Leu Cys
125                 130                 135                 140 atc ctt gga gct ggg gtc cag gcc tac agc cac tat gag atc ttc aca    541
Ile Leu Gly Ala Gly Val Gln Ala Tyr Ser His Tyr Glu Ile Phe Thr
                145                 150                 155 gag cag ttc tcc ttt aag gag gtg agg ata tgg aac cgc acc aaa gaa    589
Glu Gln Phe Ser Phe Lys Glu Val Arg Ile Trp Asn Arg Thr Lys Glu
            160                 165                 170 aat gca gag aag ttt gca gac aca gtg caa gga gag gta cag gtc tgt    637
Asn Ala Glu Lys Phe Ala Asp Thr Val Gln Gly Glu Val Gln Val Cys
        175                 180                 185 tct tcg gtc cag gag gct gtg gca ggt gca gat gtg atc atc aca gtc    685
Ser Ser Val Gln Glu Ala Val Ala Gly Ala Asp Val Ile Ile Thr Val
    190                 195                 200 acc ctg gca aca gag ccc att ttg ttt ggt gaa tgg gtg aag cca ggg    733
Thr Leu Ala Thr Glu Pro Ile Leu Phe Gly Glu Trp Val Lys Pro Gly
205                 210                 215                 220 gct cac atc aat gct gtc gga gcc agc cga cct gac tgg aga gaa ctg    781
Ala His Ile Asn Ala Val Gly Ala Ser Arg Pro Asp Trp Arg Glu Leu
                225                 230                 235 gat gat gag ctc atg aag gaa gct gtg ctg tac gtg gat tcc cag gag    829
Asp Asp Glu Leu Met Lys Glu Ala Val Leu Tyr Val Asp Ser Gln Glu
            240                 245                 250
```

```
gct gcc ctg aag gag tct gga gat gtc ctg ttg tca ggg gcc gag atc      877
Ala Ala Leu Lys Glu Ser Gly Asp Val Leu Leu Ser Gly Ala Glu Ile
        255                 260                 265 ttt gct gag ctg gga gaa gtg att aag gga gtg aag cca gcc cac tgt      925
Phe Ala Glu Leu Gly Glu Val Ile Lys Gly Val Lys Pro Ala His Cys
270                 275                 280 gag aag acc aca gtg ttc aag tct ttg gga atg gca gtg gaa gac aca      973
Glu Lys Thr Thr Val Phe Lys Ser Leu Gly Met Ala Val Glu Asp Thr
285                 290                 295                 300 gtt gca gcc aaa ctg atc tat gat tcc tgg tca tct ggt aaa tag         1018
Val Ala Ala Lys Leu Ile Tyr Asp Ser Trp Ser Ser Gly Lys
            305                 310 aacaaaggaa cttggtgttg agatggatgc tcgaggaatg ttgctgctgg ttctcataat   1078
ttctagagta aatgaggaag tccagtcccc agtgaactct cctttgtgc ttattgcgtt    1138 ttaccttaag tgctgagatc ttcatttatg tttgtagttg gaaagcaaaa ctagccattt   1198
cttctgctat accaagttat aatagcattc atttcccttt atatttccct gaaataaagc   1258
actacccaat tctgcaa                                                   1275

<210> SEQ ID NO 8
<211> LENGTH: 314
<212> TYPE: PRT
<213> ORGANISM: Macaca mulatta

<400> SEQUENCE: 8

Met Asn Arg Val Pro Ala Phe Leu Ser Ala Ala Glu Val Glu His
1               5                   10                  15

Leu Arg Ser Ser Ser Leu Leu Ile Pro Pro Leu Glu Thr Ala Leu Ala
                20                  25                  30

Asn Phe Ser Ser Gly Pro Glu Gly Gly Val Met Gln Pro Val Arg Thr
            35                  40                  45

Val Val Pro Val Thr Lys His Arg Gly Tyr Leu Gly Val Met Pro Ala
        50                  55                  60

Tyr Ser Ala Ala Glu Asp Ala Leu Thr Thr Lys Leu Val Thr Phe Tyr
65                  70                  75                  80

Glu Asp Arg Gly Ile Thr Ser Val Val Pro Ser His Gln Ala Thr Val
                85                  90                  95

Leu Leu Phe Glu Pro Ser Asn Gly Thr Leu Leu Ala Val Met Asp Gly
            100                 105                 110

Asn Val Ile Thr Ala Lys Arg Thr Ala Ala Val Ser Ala Ile Ala Thr
        115                 120                 125

Lys Phe Leu Lys Pro Pro Ser Ser Glu Val Leu Cys Ile Leu Gly Ala
130                 135                 140

Gly Val Gln Ala Tyr Ser His Tyr Glu Ile Phe Thr Glu Gln Phe Ser
145                 150                 155                 160

Phe Lys Glu Val Arg Ile Trp Asn Arg Thr Lys Glu Asn Ala Glu Lys
                165                 170                 175

Phe Ala Asp Thr Val Gln Gly Glu Val Gln Val Cys Ser Ser Val Gln
            180                 185                 190

Glu Ala Val Ala Gly Ala Asp Val Ile Ile Thr Val Thr Leu Ala Thr
        195                 200                 205

Glu Pro Ile Leu Phe Gly Glu Trp Val Lys Pro Gly Ala His Ile Asn
210                 215                 220

Ala Val Gly Ala Ser Arg Pro Asp Trp Arg Glu Leu Asp Asp Glu Leu
225                 230                 235                 240
```

```
Met Lys Glu Ala Val Leu Tyr Val Asp Ser Gln Ala Ala Leu Lys
            245                 250                 255

Glu Ser Gly Asp Val Leu Leu Ser Gly Ala Glu Ile Phe Ala Glu Leu
            260                 265                 270

Gly Glu Val Ile Lys Gly Val Lys Pro Ala His Cys Glu Lys Thr Thr
            275                 280                 285

Val Phe Lys Ser Leu Gly Met Ala Val Glu Asp Thr Val Ala Ala Lys
            290                 295                 300

Leu Ile Tyr Asp Ser Trp Ser Ser Gly Lys
305                 310

<210> SEQ ID NO 9
<211> LENGTH: 1303
<212> TYPE: DNA
<213> ORGANISM: Macaca fascicularis
<220> FEATURE:
<221> NAME/KEY: CDS
<222> LOCATION: (89)..(1033)

<400> SEQUENCE: 9
cactgttggc ctactgaaaa aatatagggc acagccgagg gtacgtggat cgcggtgcgg      60
agactgaggt tagaaggcag gtggcgag atg aac cgc gta cca gcg ttc ctg       112
                                 Met Asn Arg Val Pro Ala Phe Leu
                                   1               5 agc gcg gcc gag gtg gag gaa cac ctc cgc agc tcc agc ctc ctc atc      160
Ser Ala Ala Glu Val Glu Glu His Leu Arg Ser Ser Ser Leu Leu Ile
     10                  15                  20 ccg cct cta gag acg gcc ctg gcc aac ttc tcc agc ggt ccc gaa gga      208
Pro Pro Leu Glu Thr Ala Leu Ala Asn Phe Ser Ser Gly Pro Glu Gly
 25                  30                  35                  40 ggg gtc atg cag ccc gtg cgc acc gtg gtg ccg gtg acc aag cac agg      256
Gly Val Met Gln Pro Val Arg Thr Val Val Pro Val Thr Lys His Arg
                 45                  50                  55 ggc tac ctg ggg gtc atg ccc gcc tac agt gct gca gag gat gcc ctg      304
Gly Tyr Leu Gly Val Met Pro Ala Tyr Ser Ala Ala Glu Asp Ala Leu
             60                  65                  70 acc acc aag ttg gtc acc ttc tac gag gac cgc ggc atc acc tcg gtc      352
Thr Thr Lys Leu Val Thr Phe Tyr Glu Asp Arg Gly Ile Thr Ser Val
         75                  80                  85 gtc ccc tcc cac cag gct act gtg cta ctc ttt gag ccc agc aat ggc      400
Val Pro Ser His Gln Ala Thr Val Leu Leu Phe Glu Pro Ser Asn Gly
     90                  95                 100 acc ctg ctg gcg gtc atg gat gga aat gtc ata act gca aag aga aca      448
Thr Leu Leu Ala Val Met Asp Gly Asn Val Ile Thr Ala Lys Arg Thr
105                 110                 115                 120 gct gcg gtt tct gcc att gcc acc aag ttt ctg aaa ccc ccc agc agt      496
Ala Ala Val Ser Ala Ile Ala Thr Lys Phe Leu Lys Pro Pro Ser Ser
                125                 130                 135 gaa gtg ctg tgc atc ctt gga gct ggg gtc cag gcc tac agc cac tat      544
Glu Val Leu Cys Ile Leu Gly Ala Gly Val Gln Ala Tyr Ser His Tyr
            140                 145                 150 gag atc ttc aca gag cag ttc tcc ttt aag gag gtg agg ata tgg aac      592
Glu Ile Phe Thr Glu Gln Phe Ser Phe Lys Glu Val Arg Ile Trp Asn
        155                 160                 165 cgc acc aaa gaa aat gca gag aag ttt gca gac aca gtg caa gga gag      640
Arg Thr Lys Glu Asn Ala Glu Lys Phe Ala Asp Thr Val Gln Gly Glu
    170                 175                 180 gta cag gtc tgt tct tca gtc cag gag gct gtg gca ggt gca gat gtg      688
Val Gln Val Cys Ser Ser Val Gln Glu Ala Val Ala Gly Ala Asp Val
```

-continued

```
                185                 190                 195                 200
atc atc aca gtc acc ctg gca aca gag ccc att ttg ttt ggt gaa tgg       736
Ile Ile Thr Val Thr Leu Ala Thr Glu Pro Ile Leu Phe Gly Glu Trp
                205                 210                 215 gtg aag cca ggg gct cac atc aat gct gtc gga gcc agc cga cct gac       784
Val Lys Pro Gly Ala His Ile Asn Ala Val Gly Ala Ser Arg Pro Asp
                220                 225                 230 tgg aga gaa ctg gat gat gag ctc atg aag gaa gct gtg ctg tac gtg       832
Trp Arg Glu Leu Asp Asp Glu Leu Met Lys Glu Ala Val Leu Tyr Val
                235                 240                 245 gat tcc cag gag gct gcc ctg aag gag tct gga gat gtc ctg ttg tca       880
Asp Ser Gln Glu Ala Ala Leu Lys Glu Ser Gly Asp Val Leu Leu Ser
                250                 255                 260 ggg gcc gag atc ttt gct gag ctg gga gaa gtg att aag gga gtg aag       928
Gly Ala Glu Ile Phe Ala Glu Leu Gly Glu Val Ile Lys Gly Val Lys
265                 270                 275                 280 cca gcc cac tgt gag aag acc aca gtg ttc aag tct ttg gga atg gca       976
Pro Ala His Cys Glu Lys Thr Thr Val Phe Lys Ser Leu Gly Met Ala
                285                 290                 295 gtg gaa gac aca gtt gca gcc aaa ctg atc tat gat tcc tgg tca tct      1024
Val Glu Asp Thr Val Ala Ala Lys Leu Ile Tyr Asp Ser Trp Ser Ser
                300                 305                 310 ggt aaa tag aacaaggaa cttggtgttg agatggatgc tcgaggaatg              1073
Gly Lys ttgctgctgg ttctcataat ttctagagta aatgaggaag tccagtcccc agtgaactct    1133
ccttttgtgc ttattgcgtt ttaccttaag tgctgagatc ctcatttatg tctgtagttg   1193
gaaagcaaaa ctagccattt cttctgctat accaagttat aatagcattc atttcccttt   1253
atatttccct gaaataaagc actacccaat tctgaaaaaa aaaaaaaaaa              1303
```

<210> SEQ ID NO 10
<211> LENGTH: 314
<212> TYPE: PRT
<213> ORGANISM: Macaca fascicularis

<400> SEQUENCE: 10

```
Met Asn Arg Val Pro Ala Phe Leu Ser Ala Ala Glu Val Glu Glu His
1               5                   10                  15

Leu Arg Ser Ser Ser Leu Leu Ile Pro Pro Leu Glu Thr Ala Leu Ala
                20                  25                  30

Asn Phe Ser Ser Gly Pro Glu Gly Gly Val Met Gln Pro Val Arg Thr
            35                  40                  45

Val Val Pro Val Thr Lys His Arg Gly Tyr Leu Gly Val Met Pro Ala
        50                  55                  60

Tyr Ser Ala Ala Glu Asp Ala Leu Thr Thr Lys Leu Val Thr Phe Tyr
65                  70                  75                  80

Glu Asp Arg Gly Ile Thr Ser Val Val Pro Ser His Gln Ala Thr Val
                85                  90                  95

Leu Leu Phe Glu Pro Ser Asn Gly Thr Leu Leu Ala Val Met Asp Gly
                100                 105                 110

Asn Val Ile Thr Ala Lys Arg Thr Ala Ala Val Ser Ala Ile Ala Thr
            115                 120                 125

Lys Phe Leu Lys Pro Pro Ser Ser Glu Val Leu Cys Ile Leu Gly Ala
        130                 135                 140

Gly Val Gln Ala Tyr Ser His Tyr Glu Ile Phe Thr Glu Gln Phe Ser
145                 150                 155                 160
```

```
Phe Lys Glu Val Arg Ile Trp Asn Arg Thr Lys Glu Asn Ala Glu Lys
                165                 170                 175

Phe Ala Asp Thr Val Gln Gly Glu Val Gln Val Cys Ser Ser Val Gln
            180                 185                 190

Glu Ala Val Ala Gly Ala Asp Val Ile Ile Thr Val Thr Leu Ala Thr
        195                 200                 205

Glu Pro Ile Leu Phe Gly Glu Trp Val Lys Pro Gly Ala His Ile Asn
    210                 215                 220

Ala Val Gly Ala Ser Arg Pro Asp Trp Arg Glu Leu Asp Asp Glu Leu
225                 230                 235                 240

Met Lys Glu Ala Val Leu Tyr Val Asp Ser Gln Glu Ala Ala Leu Lys
                245                 250                 255

Glu Ser Gly Asp Val Leu Leu Ser Gly Ala Glu Ile Phe Ala Glu Leu
            260                 265                 270

Gly Glu Val Ile Lys Gly Val Lys Pro Ala His Cys Glu Lys Thr Thr
        275                 280                 285

Val Phe Lys Ser Leu Gly Met Ala Val Glu Asp Thr Val Ala Ala Lys
    290                 295                 300

Leu Ile Tyr Asp Ser Trp Ser Ser Gly Lys
305                 310

<210> SEQ ID NO 11
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 11
uccaagcuca gcaaagaugu cagcc                                          25

<210> SEQ ID NO 12
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 12
uaacuuggug gugagcgcau ccuca                                          25

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
cagatgtgcg tcaggcgttc                                                20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
tagtgatgct gggcactgcg                                                20
```

```
<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
atgcgctcac caccaagtta                                                    20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
atttccatcc atgaccgcca                                                    20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
gcggcggagg agagctaaaa                                                    20

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
ggcagcattc ataccttggg c                                                  21

<210> SEQ ID NO 19
<211> LENGTH: 23
<212> TYPE: DNA
<213> ORGANISM: Artificial Sequence
<220> FEATURE:
<223> OTHER INFORMATION: primer

<400> SEQUENCE: 19
taatgaagga cttggcggat gag                                                23

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
cagcagcttg cagtgtggac                                                    20

<210> SEQ ID NO 21
<211> LENGTH: 20
<212> TYPE: DNA
<213> ORGANISM: Artificial Sequence
<220> FEATURE:
<223> OTHER INFORMATION: primer
```

```
<400> SEQUENCE: 21
tcctgcctga ccgcttagtg                                                   20

<210> SEQ ID NO 22
<211> LENGTH: 23
<212> TYPE: DNA
<213> ORGANISM: Artificial Sequence
<220> FEATURE:
<223> OTHER INFORMATION: primer

<400> SEQUENCE: 22
gcgtgtctac aaactctgac agg                                               23

<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
cccggtggat gtggtaaaga c                                                 21

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24
caagctccca gacgcagaaa g                                                 21

<210> SEQ ID NO 25
<211> LENGTH: 25
<212> TYPE: DNA
<213> ORGANISM: Artificial Sequence
<220> FEATURE:
<223> OTHER INFORMATION: primer

<400> SEQUENCE: 25
cttcatctgg taacacaaga ggtgc                                             25

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
ttctgggcct cgattcgctc                                                   20

<210> SEQ ID NO 27
<211> LENGTH: 21
<212> TYPE: DNA
<213> ORGANISM: Artificial Sequence
<220> FEATURE:
<223> OTHER INFORMATION: primer

<400> SEQUENCE: 27
ccctaaaggc aggctctctc a                                                 21

<210> SEQ ID NO 28
<211> LENGTH: 20
```

```
<212> TYPE: DNA
<213> ORGANISM: Artificial Sequence
<220> FEATURE:
<223> OTHER INFORMATION: primer

<400> SEQUENCE: 28
tccccgaaaa cggccatctc                                              20

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
aagagtcccg aacgaggctg                                              20

<210> SEQ ID NO 30
<211> LENGTH: 21
<212> TYPE: DNA
<213> ORGANISM: Artificial Sequence
<220> FEATURE:
<223> OTHER INFORMATION: primer

<400> SEQUENCE: 30
actcacagac ccttactggc a                                            21
```